(12) United States Patent
Bambot et al.

(10) Patent No.: US 8,644,912 B2
(45) Date of Patent: Feb. 4, 2014

(54) SYSTEM AND METHOD FOR DETERMINING TISSUE CHARACTERISTICS

(75) Inventors: Shabbir Bambot, Suwanee, GA (US); Mark L. Faupel, Alpharetta, GA (US); Anant Agrawal, Atlanta, GA (US); Keith D. Ignotz, Duluth, GA (US); Andrew Fordham, Sugar Hill, GA (US)

(73) Assignee: SpectRx, Inc., Norcross, GA (US)

( * ) Notice: Subject to any disclaimer, the term of this patent is extended or adjusted under 35 U.S.C. 154(b) by 0 days.

(21) Appl. No.: 13/214,638

(22) Filed: Aug. 22, 2011

(65) Prior Publication Data

US 2011/0306887 A1  Dec. 15, 2011

Related U.S. Application Data

(60) Continuation of application No. 12/099,876, filed on Apr. 9, 2008, now abandoned, and a continuation of application No. 10/647,222, filed on Aug. 26, 2003, now abandoned, and a continuation-in-part of application No. 10/611,917, filed on Jul. 3, 2003, now Pat. No. 7,006,220, and a continuation-in-part of application No. 10/603,597, filed on Jun. 26, 2003, now Pat. No. 6,975,899, and a continuation-in-part of application No. 10/446,857, filed on May 29, 2003, now Pat. No. 6,870,620, and a continuation-in-part of application No. 10/337,687, filed on Jan. 8, 2003, now abandoned, and a continuation-in-part of application No. PCT/US02/06350, filed on Mar. 1, 2002, and a continuation of application No. 09/786,781, filed on Mar. 9, 2001, now abandoned, application No. 13/214,638, which is a continuation of application No. 09/700,538, filed on Nov. 16, 2000, now Pat. No. 6,590,651, and a division of application No. 09/533,817, filed on Mar. 24, 2000, now Pat. No. 6,577,391, and a continuation of application No. 09/434,518, filed on Nov. 5, 1999, now abandoned, which is a continuation-in-part of application No. PCT/US99/20646, filed on Sep. 10, 1999, and a continuation-in-part of application No. PCT/US99/10947, filed on May 19, 1999.

(60) Provisional application No. 60/272,458, filed on Mar. 2, 2001, provisional application No. 60/126,056, filed on Mar. 23, 1999.

(51) Int. Cl.
*A61B 6/00* (2006.01)

(52) U.S. Cl.
USPC ............ 600/476; 600/407; 600/473; 600/478

(58) Field of Classification Search
USPC .................................. 600/407, 473, 476, 478
See application file for complete search history.

(56) References Cited

U.S. PATENT DOCUMENTS

| | | | |
|---|---|---|---|
| 4,534,360 A * | 8/1985 | Williams | ...................... 600/473 |
| 6,364,829 B1 | 4/2002 | Fulghum | |
| 6,571,118 B1 | 5/2003 | Utzinger et al. | |

FOREIGN PATENT DOCUMENTS

WO      WO 00/15101        3/2000

OTHER PUBLICATIONS

Shabbir B. Bambot et al., "Sensing oxygen through skin using a red diode laser and fluorescence liftetimes", Biosens and Bioelectronics, vol. 10, Nov. 6/7, pp. 643-652, 1995.

Kevin T. Shoemacher et al., "Ultraviolet Laser-Induced Fluorescence of Colonic Tissues: Basic Biology and Diagnostic Potential", Laser in Surgery Medicine, vol. 12, pp. 63-78, 1992.

(Continued)

*Primary Examiner* — Peter Luong
(74) *Attorney, Agent, or Firm* — Altera Law Group, LLC

(57) ABSTRACT

An apparatus to interrogate, receive, and analyze full emission spectra for at least one fluorescence excitation wavelength and for at least one reflectance measurement to determine tissue characteristics. The apparatus includes a base unit having illumination, detection and control sub-units, the illumination sub-unit providing illumination optical energy for illuminating a target tissue and the detection sub-unit detecting tissue characteristics of a target tissue, a separate tissue interface unit, and a pathway coupling the base unit and the tissue interface unit. The system and apparatus may also include a tube for maintaining the distance between the tissue and units and for surrounding the tissue to prevent patient movement from being transmitted to the tissue.

25 Claims, 24 Drawing Sheets

(56) References Cited

OTHER PUBLICATIONS

Charles E. Alpers et al., "The Prevalance of Carcinoma in Situ in Normal and Cancer Associated Breasts", Human Pathology, vol. 16, No. 8, pp796-807, Aug. 1985.

Danely Slaughter et al., Field Cancerization in Oral Stratified Squamour Epithelium: Clinical Implication of Multicentric Origin Cancer, vol. 6, No. 4, pp. 963-968, 1953.

Cancer Diagnostics: The World Markets, Clinical Reports, PJB Publications, p. 72, 1997.

* cited by examiner

| # | Measurement | Excitation | Collection | Spectro-graph center λ | Meas. time secs. |
|---|---|---|---|---|---|
| 1 | Flourescence | 350 nm (10 nm BP) | 385 nm LP (GG 385) | 450nm | 2 |
| 2 | Flourescence | 400 nm (10 nm BP) | 420 nm LP (GG 485) | 500nm | 2 |
| 3 | Flourescence | 460 nm (10 nm BP) | 495 nm LP (GG 495) | 560nm | 4 |
| 4 | Reflectance | OD1.5 ND filter | 300-700 nm bp (BG 26) | 500nm | 0.2 |

BP=bandpass
LP=Long-pass

| Measurement | Mask Position | Exposure Time | Excitation Filter | Spectrograph Center λ | Collection Filter | Safety Shutter Open |
|---|---|---|---|---|---|---|
| 1 | 1 | 0.2 | ND 1.5 | 580 | WG-320 | No |
| 2 | 2 | 0.2 | ND 1.5 | 560 | WG-320 | No |
| 3 | 3 | 0.2 | ND 1.5 | 540 | WG-320 | No |
| 4 | 4 | 0.2 | ND 1.5 | 520 | WG-320 | No |
| 5 | 5 | 0.2 | ND 1.5 | 500 | WG-320 | No |
| 6 | 6 | 0.2 | ND 1.5 | 480 | WG-320 | No |
| 7 | 7 | 0.2 | ND 1.5 | 460 | WG-320 | No |
| 8 | 8 | 0.2 | ND 1.5 | 440 | WG-320 | No |

FIG. 22

| Measurement | Mask Position | Exposure Time | Excitation Filter | Spectrograph Center λ | Collection Filter | Safety Shutter Open |
|---|---|---|---|---|---|---|
| 1 | 1 | 0.2 | ND 1.5 | 580 | WG-320 | No |
| 2 | 1 | 0.2 | ND 1.5 | 580 | WG-320 | Yes |
| 3 | 2 | 0.2 | ND 1.5 | 560 | WG-320 | Yes |
| 4 | 3 | 0.2 | ND 1.5 | 540 | WG-320 | Yes |
| 5 | 4 | 0.2 | ND 1.5 | 520 | WG-320 | Yes |
| 6 | 5 | 0.2 | ND 1.5 | 500 | WG-320 | Yes |
| 7 | 6 | 0.2 | ND 1.5 | 480 | WG-320 | Yes |
| 8 | 7 | 0.2 | ND 1.5 | 460 | WG-320 | Yes |
| 9 | 8 | 0.2 | ND 1.5 | 440 | WG-320 | Yes |

FIG. 23

| Measurement | Mask Position | Exposure Time | Excitation Filter | Spectrograph Center λ | Collection Filter | Safety Shutter Open |
|---|---|---|---|---|---|---|
| 1 | 1 | 4 | 350-20 | 580 | GG385 | No |
| 2 | 1 | 4 | 350-20 | 580 | GG385 | Yes |
| 3 | 2 | 4 | 350-20 | 560 | GG385 | Yes |
| 4 | 3 | 4 | 350-20 | 540 | GG385 | Yes |
| 5 | 4 | 4 | 350-20 | 520 | GG385 | Yes |
| 6 | 5 | 4 | 350-20 | 500 | GG385 | Yes |
| 7 | 6 | 4 | 350-20 | 480 | GG385 | Yes |
| 8 | 7 | 4 | 350-20 | 460 | GG385 | Yes |
| 9 | 8 | 4 | 350-20 | 440 | GG385 | Yes |
| 10 | 1 | 2 | 400-20 | 580 | GG435 | No |
| 11 | 1 | 2 | 400-20 | 580 | GG435 | Yes |
| 12 | 2 | 2 | 400-20 | 560 | GG435 | Yes |
| 13 | 3 | 2 | 400-20 | 540 | GG435 | Yes |
| 14 | 4 | 2 | 400-20 | 520 | GG435 | Yes |
| 15 | 5 | 2 | 400-20 | 500 | GG435 | Yes |
| 16 | 6 | 2 | 400-20 | 480 | GG435 | Yes |
| 17 | 7 | 2 | 400-20 | 460 | GG435 | Yes |
| 18 | 8 | 2 | 400-20 | 440 | GG435 | Yes |
| 19 | 1 | 2 | 460-20 | 580 | GG495 | No |
| 20 | 1 | 2 | 460-20 | 580 | GG495 | Yes |
| 21 | 2 | 2 | 460-20 | 560 | GG495 | Yes |
| 22 | 3 | 2 | 460-20 | 540 | GG495 | Yes |
| 23 | 4 | 2 | 460-20 | 520 | GG495 | Yes |
| 24 | 5 | 2 | 460-20 | 500 | GG495 | Yes |
| 25 | 6 | 2 | 460-20 | 480 | GG495 | Yes |
| 26 | 7 | 2 | 460-20 | 460 | GG495 | Yes |
| 27 | 8 | 2 | 460-20 | 440 | GG495 | Yes |

FIG. 24

SYSTEM AND METHOD FOR DETERMINING TISSUE CHARACTERISTICS

This application is a Continuation of U.S. patent application Ser. No. 12/099,876, Apr. 9, 2008, Pending, is a Continuation of U.S. patent application Ser. No. 10/647,222, Aug. 26, 2003, Abandoned, is a Continuation in part of U.S. patent application Ser. No. 10/611,917, Jul. 3, 2003, U.S. Pat. No. 7,006,220, is a Continuation-in-part of U.S. patent application Ser. No. 10/603,597, Jun. 26, 2003, U.S. Pat. No. 6,975,899, is a Continuation-in-part of U.S. patent application Ser. No. 10/446,857, May 29, 2003, U.S. Pat. No. 6,870,620, is a Continuation-in-part of U.S. patent application Ser. No. 10/337,687, Jan. 8, 2003, Abandoned, is a Continuation-in-part of PCT/US02/06350, Mar. 1, 2002, Expired, is a continuation of U.S. patent application Ser. No. 09/786,781, Mar. 9, 2001, Abandoned, Claims Priority from Provisional Application 60/272,458, Mar. 2, 2001, Expired, is a continuation of U.S. patent application Ser. No. 09/700,538, Nov. 16, 2000, U.S. Pat. No. 6,590,651, is a Division of U.S. patent application Ser. No. 09/533,817, Mar. 24, 2000, U.S. Pat. No. 6,577,391, is a continuation of U.S. patent application Ser. No. 09/434,518, Nov. 5, 1999, Abandoned, is Continuation-in-part of PCT/US99/20646, Sep. 10, 1999, Expired, is Continuation-in-part of PCT/US99/10947, May 5, 1999, Expired, Claims Priority from Provisional Application 60/126,056, Mar. 23, 1999, Expired. The applications are incorporated herein by reference.

BACKGROUND OF THE INVENTION

1. Field of the Invention

The invention relates to an apparatus and methods for determining tissue characteristics of, for example, biological tissue.

SUMMARY OF THE INVENTION

The present invention, according to its various embodiments, provides for a method and apparatus that interrogates, receives and analyzes full emission spectra for at least one fluorescence excitation wavelength and for at least one reflectance measurement to determine tissue characteristics.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings, in which like reference numerals refer to like elements, and wherein:

FIGS. 22-23 are tables of instrument settings for each of eight software driven measurements that account for each of eight column positions on a target; and FIG. 24 is a table of instrument settings for measurements made in three sets using a different excitation and emission wavelength for each set.

DETAILED DESCRIPTION OF INVENTION

Before the present systems, methods and apparatus are disclosed and described, it is to be understood that the terminology used herein is for the purpose of describing particular embodiments only and is not intended to be limiting. It must be noted that, as used in the specification and the appended claims, the singular forms "a", "an" and "the" include plural referents unless the context clearly dictates otherwise.

Ranges may be expressed herein as from "about" or "approximately" one particular value and/or to "about" or "approximately" another particular value. When such a range is expressed, another embodiment comprises from the one particular value and/or to the other particular value. Similarly, when values are expressed as approximations, by use of the antecedent "about," it will be understood that the particular value forms another embodiment.

Various embodiments of the present invention include systems, methods and apparatus that may be utilized to determine tissue characteristics by applying and measuring optical energy, including but not limited to visible, infrared and/or UV light. It should be understood that the term "illumination" according to the invention means "to give optical energy to", the term optical energy again, including but not limited to visible, infrared and/or UV light.

In several embodiments, the present invention comprises a base unit, a tissue interface unit and a pathway that couples the base unit and the tissue interface unit. In one particular embodiment, the present invention is comprised of a tissue interface unit that is optically and electronically coupled to a base unit, as shown in FIGS. 1A-1B.

Figure 1A:
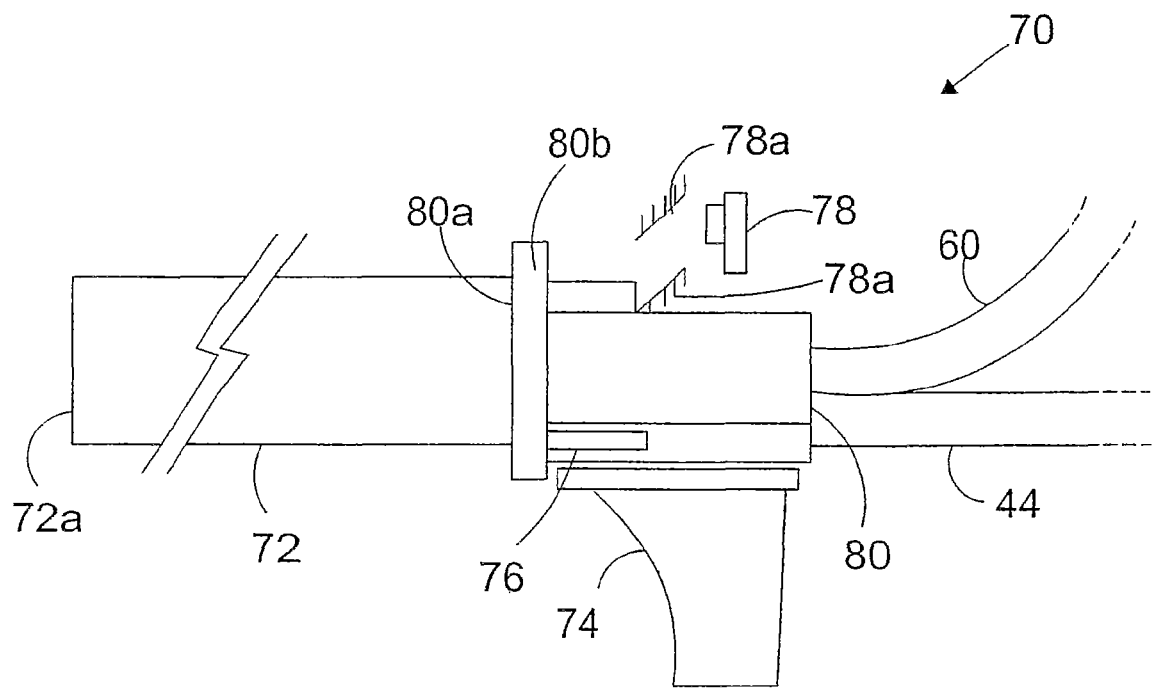
FIG. 1A is a schematic side view of a tissue interface unit of a system for determining tissue characteristics according to one embodiment of the invention.
Figure 1B:
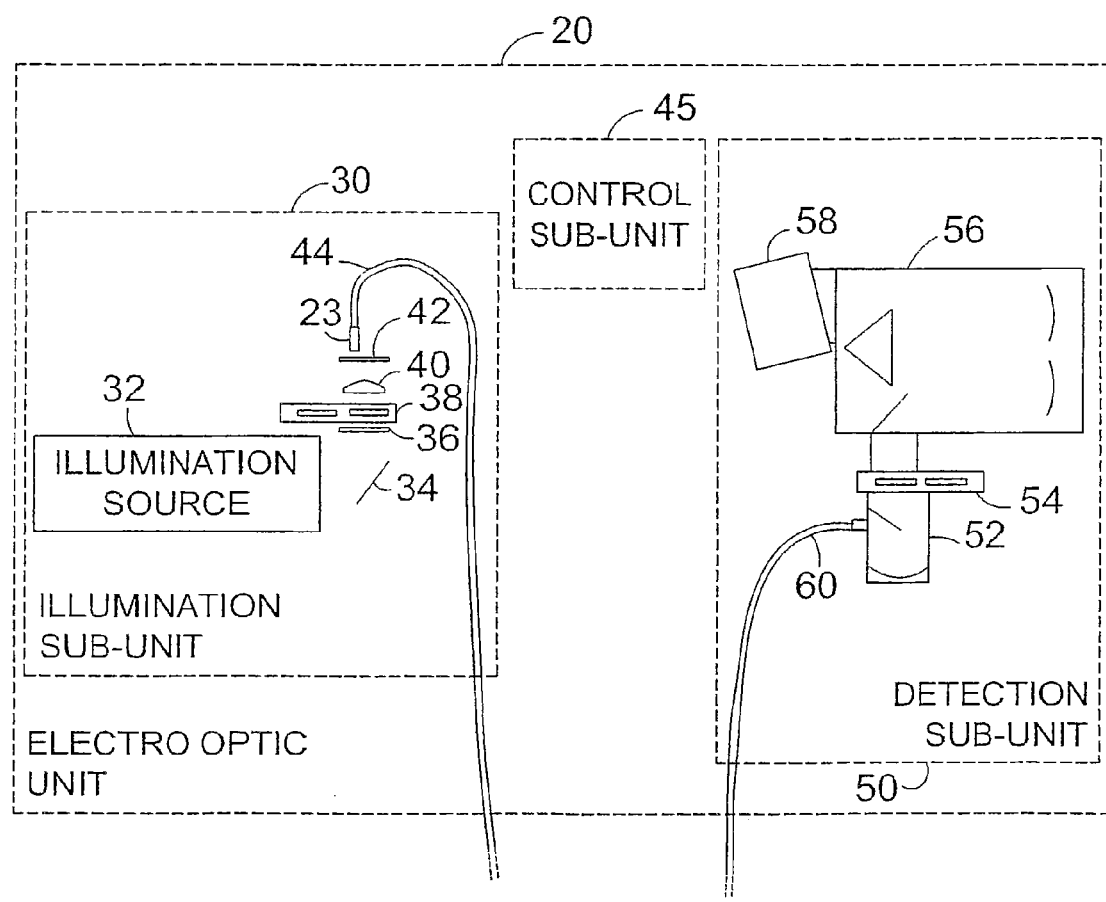
FIG. 1B is a schematic diagram of a base unit of a system for determining tissue characteristics according to one embodiment of the invention.

FIG. 1A is a schematic side view drawing of a tissue interface unit according to an embodiment of the present invention. The tissue interface unit 70 includes a base structure 80. The base structure 80 may include a handle 74 attached thereto and configured to be graspable by a user; however, other configurations may also be appropriate.

A tube 72 may be configured to be removably attachable to the base structure 80. The tube 72 functions as a barrier to exclude, for example, room light. The tube 72 is not necessarily tubular or cylindrical in shape; other configurations may also be appropriate.

Figure 2:
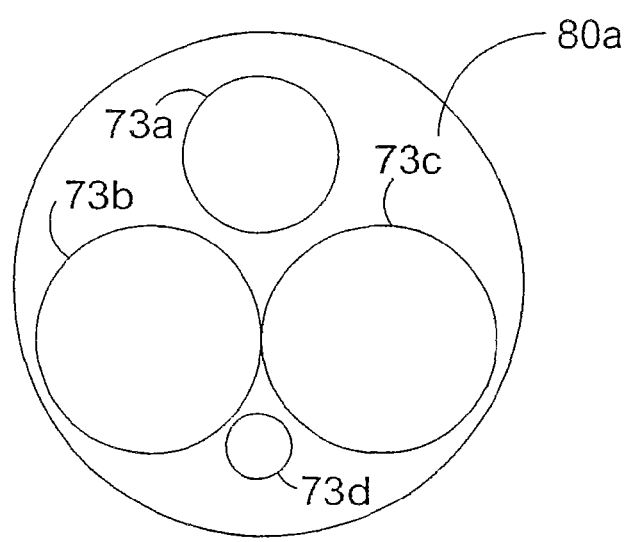
FIG. 2 is a front view of an end plate of a body structure of the tissue interface unit of FIG. 1A.

The tube 72 connects to base structure 80 via plate 80*b*. An end face 80*a* of plate 80*b* is shown in FIG. 2. The end face 80*a* contains at least one opening for respective pathways 73*a*, 73*b*, 73*c*, 73*d*. These pathways are connected to and selectively share the tube 72 in such a way that no interference occurs between the respective pathways. For example, illumination pathway 73*b* delivers to a subject tissue illumination energy or light received from the base unit 20 along illumination pathway 44. The collection pathway 73*c* receives energy or light reflected and/or emitted by a subject tissue and guides it to collection pathway 60, which guides the collected light to the base unit 20.

The tissue interface unit 70 may further include an illumination source 76 and a second illumination pathway 73*d*. Additionally, the tissue interface unit 70 may include an imaging device 78 and an imaging pathway 73*a*. The imaging device could take the form of a digital camera, or a CCD based imaging device, although other imaging devices could also be used. The second illumination pathway 73*d* delivers illumination energy or light from the illumination source 76 to the subject tissue. This illumination energy or light is reflected off the subject tissue as image energy or light. The image energy or light is received into the imaging pathway 73*a* where it is directed to an imaging device 78. The imaging device is then used to provide a user with an image of all or a portion of the subject tissue.

The second illumination pathway 73*d* and the imaging device 78 comprise the imaging channel (not shown). The imaging device 78 allows the user to position the distal end 72*a* of the tube 72 in the proper and otherwise desired contact with the tissue and to verify that such contact has been accomplished. Moreover, the imaging channel allows the user to acquire a digital or other image of the tissue with the help of the imaging device 78. This image can serve as an additional visual tissue diagnosis tool.

The tissue interface unit 70 may also contain various lens assemblies (not shown) that direct optical energy from the illumination pathways 73*b*, 73*d* onto the subject tissue, and that direct energy or light from the subject tissue into the collection pathway 73*c* and the imaging pathway 73*a*. For example, the various lens assemblies may comprise a set of achromatic lens doublets. The matched set of achromatic lens doublets may be provided in each pathway. The doublets are generally those commonly used in the art, such as a BK7/SF2 glass biconvex/planoconcave combination available off the shelf from Edmund Scientific, OptoSigma and Melles Griot; although other lenses may also be appropriate. The material of the lenses may be used to limit irradiation and collection in the UV to a desired wavelength range, such as for example a minimum wavelength of approximately 350 nm wavelength range. According to embodiments of the present invention, the lenses may provide magnification/demagnification in the excitation/collection paths, respectively.

The tube 72 can function to fix the lens assemblies a predetermined distance from the subject tissue. In addition, if the subject tissue is surrounded by the end 72*a* of the tube 72, the tube can function to exclude ambient optical energy from illuminating the subject tissue. The tube makes contact with the tissue setting the focal distance so the tissue to lens distance is correct.

Figure 1C:
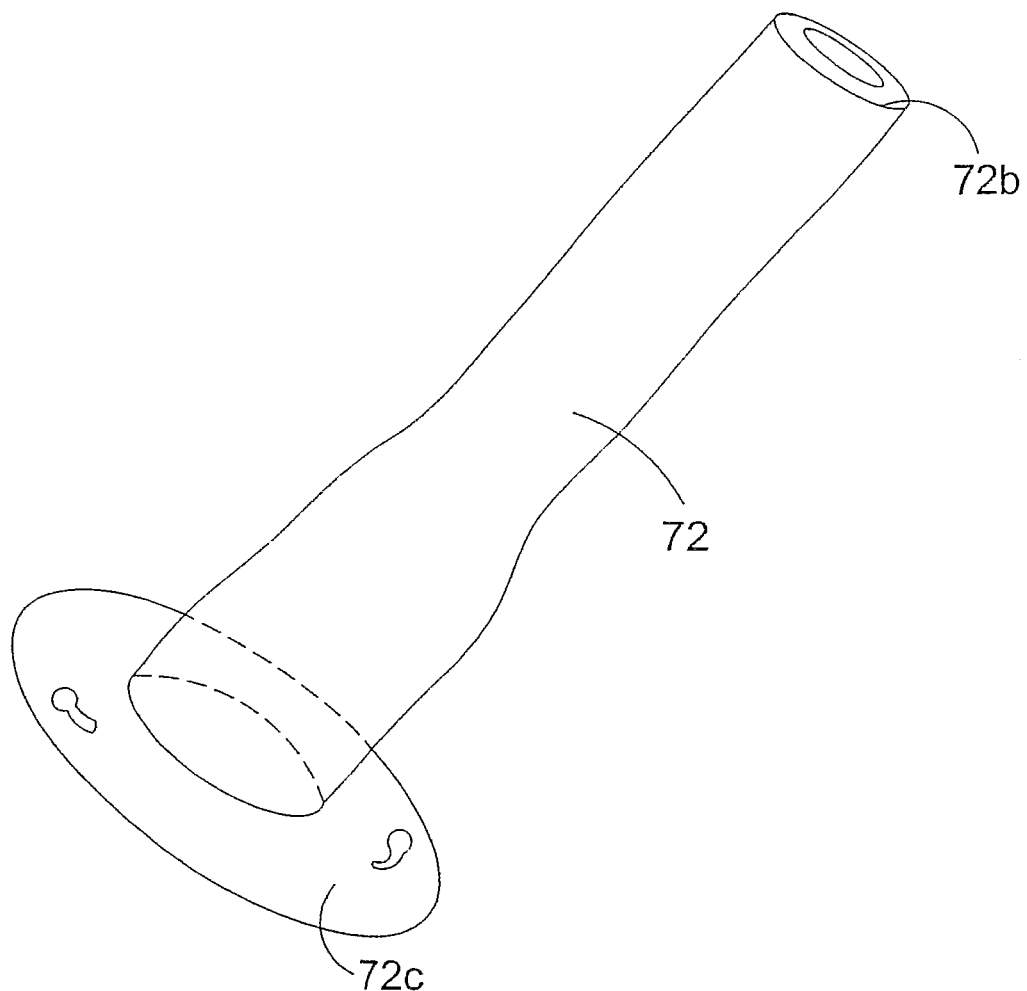
FIG. 1C is a schematic diagram of a tube according to one embodiment of the invention having a clear annulus at a distal end thereof.

The illumination pathway 73*b* may include, for example, a custom designed bundle of optical fibers. In one example, 52 optical fibers approximately 2 meters long, having a numerical aperture (NA) of approximately 0.12, and having a core diameter of approximately 100 μm is utilized to form the illumination pathway 73*b*. This fiber bundle may be only part of the illumination pathway. The illumination pathway may also have lenses. According to one embodiment, the tube 72 comprises a clear annulus 72*b* at a distal end thereof opposite to an end plate 72*c* that allows the tube 72 to be attached, removably according to certain embodiments, to the base structure 80, as shown in FIG. 1C. Contact of the tube 72 to the surface of the tissue will be visible through the annulus 72*b*, which provides the user with visual confirmation that the tube 72 is properly positioned.

Figures 3, 6:
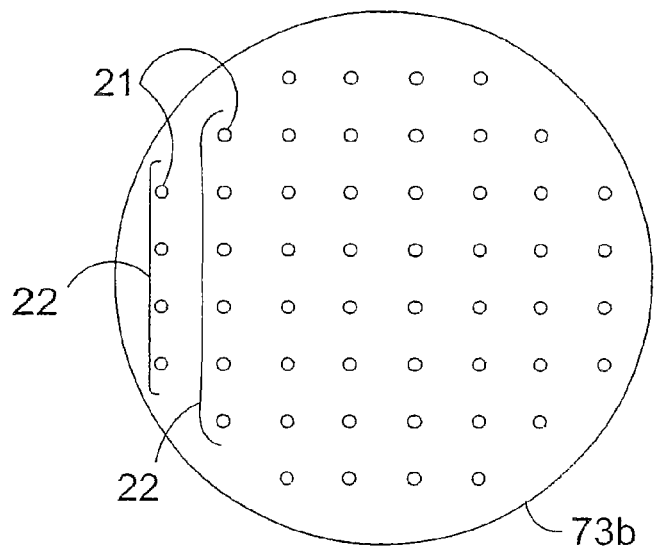
FIG. 3 shows an exemplary arrangement of illumination optical fibers on an end plate of a body structure of a tissue interface unit according to one embodiment of the invention.
FIG. 6 is a chart of exemplary spectrographic measurements to be taken to determine tissue characteristics according to one embodiment of the invention.
Figure 4:
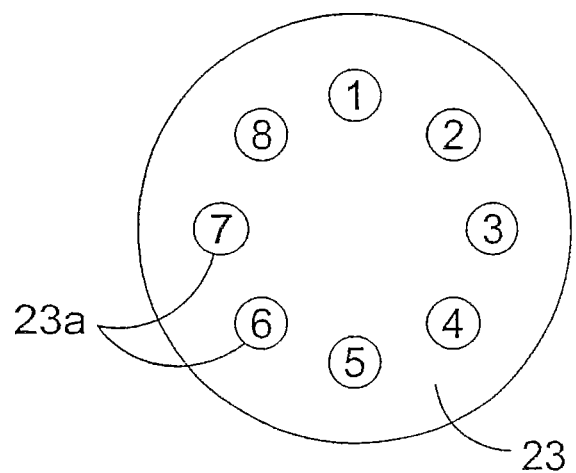
FIG. 4 shows an exemplary arrangement of bundles of optical fibers located at one end of an illumination pathway adjacent an illumination unit according to one embodiment of the invention.

One exemplary arrangement of optical fibers is illustrated in FIG. 3. The tissue end of the optical fiber bundle is held in the tissue interface unit 70 behind a pair of achromatic lens doublets (not shown). At the tissue end, the optical fibers 21 are arranged as shown in FIG. 3, in 8 columns 22. At the opposite end of the illumination pathway 44, the optical fibers 21 for each column 22 shown in FIG. 3 may be collected into a separate bundle 23*a*, as shown in FIG. 4. This means that there will be eight bundles 23 of optical fibers 21 at the opposite end of the illumination pathway. When constructed in this manner, if optical energy is fed into a single bundle 23*a* at a time, a single column 22 of optical fibers 21 will illuminate the target tissue, as discussed below in detail.

The collection pathway 73c may be, for example, another custom designed coherent bundle of optical fibers. In one example, several thousand, e.g. 5000, optical fibers that were approximately 2 meters long, having a NA of approximately 0.12, and having a core diameter of approximately 50 μm were arranged in an approximately 5-mm diameter aperture, in a coherent fashion, to provide a one to one image transfer from the tissue interface unit to the detection sub-unit of the base unit. The tissue end of the bundle of optical fibers is held in the tissue interface unit behind a pair of achromatic lens doublets. Since one column of spots is illuminated on the tissue, for example, cervix, at a time, as is later discussed, returned radiation from the same column is transferred by the coherent bundle to the detection sub-unit of the base unit. This returned radiation, which will be arranged in a column of spots, acts as a virtual vertical slit that is then spectrally resolved in the horizontal dimension by the detection sub-unit of the base unit, as is later discussed.

As mentioned above, some embodiments of the device may include an illumination device 76 and image detector 78. Together, these items allow the device operator to obtain a real-time image of the target tissue, which can help to properly orient the tissue interface unit with respect to the target tissue. These items are not required in all embodiment of the invention, and could be completely eliminated. In other embodiments of the invention, these items could be replaced with a sighting mechanism which simply allows the device operator to look down the tube 72 to view the target tissue.

In embodiments of the invention that include an illumination device 76 and imaging device 78, the illumination source 76 may be, for example, a 4.25V or 2 W halogen lamp manufactured by Welch Allyn, Inc. in Skeneateles, N.Y. This exemplary lamp has an integrated parabolic reflector that projects the optical energy onto the tissue and provides a uniform illumination on the tissue. The imaging device 78 may be, for example, a ¼" format Panasonic color board camera with 480 horizontal TV lines. This camera has a C mount adaptor, into which a focusing lens doublet may be mounted. The camera may be mounted offset from the illumination and collection pathways due to space constraints, and the image transfer accomplished using a pair of reflectors 78a.

The tissue interface unit may be designed in conjunction with a vaginal speculum configured for insertion into a patient's vagina during the examination procedure. The unit is held fixed with respect to the vaginal speculum (not shown) according to certain embodiments. However, according to other embodiments, the unit may be used without such a speculum.

Prior to conducting tissue measurements, some embodiments of the instrument may be calibrated by making one or more measurements on a disposable calibration target 78a that mounts on the distal tissue end of the tube 72. This disposable calibration target could be used to take a reference or a calibration measurement, or possibly both. Moreover, in various embodiments, these measurements may be a reflectance and/or fluorescent measurements.

FIG. 1B is a schematic diagram of a base unit according to one embodiment of the invention. The base unit 20 according to the invention is small enough to be portable or mobile. For example, the base unit 20 could be provided on a movable cart (not shown).

The base unit 20 comprises an illumination sub-unit 30, a detection sub-unit 50 and a control sub-unit 45.

The illumination sub-unit 30 includes an illumination source 32. For example, the illumination source may be a 175 W short arc Xe lamp provided with an integrated parabolic reflector, which produces a near collimated beam. Such a lamp is manufactured by ORC lighting products, a division of PerkinElmer Optoelectronics (Azusa, Calif.). Other lamps may also be appropriate. In addition, the illumination source 32 could also take the form of one or more lasers or LEDs. The illumination source 32 may be housed inside a fan cooled heat sink assembly (not shown) to limit dissipation of heat to the illumination sub-unit's other components.

Optically coupled to the illumination source 32 is an illumination filter wheel 38. The illumination filter wheel 38 provides for selective wavelength filtering and may be motorized. For example, the illumination filter wheel may be an eight-position filter wheel manufactured by ISI Systems (Santa Barbara, Calif.). An example of filters that could be used in one embodiment of the invention are listed in FIG. 6. The illumination filter wheel is mounted within the illumination sub-unit 30, as shown in FIG. 1B, and the control unit 45 selects the appropriate filter to be brought into the light path.

A cold mirror 34 may be provided between the illumination source 32 and the illumination filter wheel 38. In another embodiment of the invention, an IR absorbing glass/filter may be used instead of a cold mirror. A near collimated light beam from the illumination source 32 is directed through the filter. For example, in one embodiment of the invention, Applicants utilized a KGI glass filter available off the shelf from Melles Griot. The filter transmitted wavelengths in the range of approximately 340-700 nm. Because of its high absorption of IR wavelengths, the filter helps protect downstream components from excessive heat and also minimizes stray light in the detection sub-unit.

The illumination sub-unit 30 may also include a safety shutter 36, in particular where a continuously operating illumination source is utilized. In such a case, illumination would only be allowed into the unit and through to the tissue for the duration of the spectroscopic measurements, even though the illumination source would be continuously operating. Software in the control unit 45 would control actuation of the normally closed shutter.

The illumination sub-unit 30 may also include a focusing lens 40, for example, a single approximately 28 mm diameter, approximately 100 mm FL, plano-convex lens. The focusing lens 40 focuses the illumination optical energy or light onto the illumination pathway 44.

A mask 42, motorized using an encoded stepper motor (not shown) and controlled by the control sub-unit 45, may be provided at an entrance to the illumination pathway 44. The mask 42 is used to control the optical energy so that the optical energy will only pass into certain portions of the illumination pathway, for example, into certain ones of the optical fibers, at any given time. The mask 42 blocks the illumination optical energy from entering the remaining portions of the illumination pathway, for example, certain remaining optical fibers.

Figure 5:
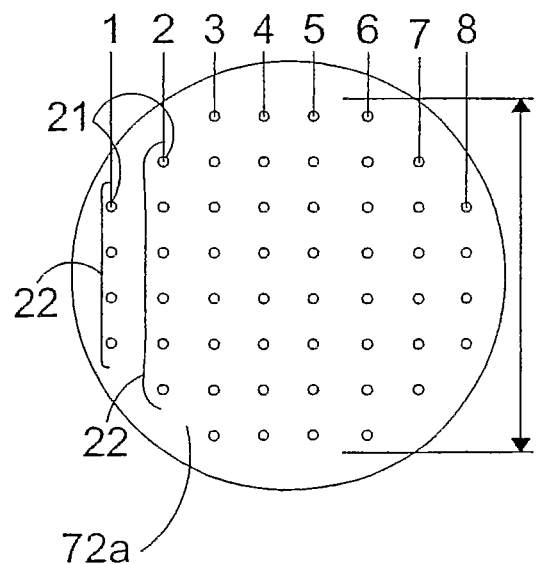
FIG. 5 shows an exemplary columnar arrangement of illumination optical fibers on an end plate of a body structure of a tissue interface unit according to one embodiment of the invention.

By way of an example, one embodiment of the illumination sub-unit end 23 of the illumination pathway 44 is shown in FIG. 4. As previously discussed, it has a collection of eight bundles 23a of optical fibers, where the optical fibers in each bundle 23a corresponding to different respective columns 22 of individual optical fibers at the tissue end 80a of the illumination pathway 44, as shown in FIG. 5. Thus, the optical fibers in bundle number 1 at the illumination sub-unit end of the illumination pathway 44, as shown in FIG. 4, correspond to the optical fibers 21 arranged in column 1 of the tissue end 80a, as shown in FIG. 5.

The mask 42 has a single hole (not shown) that can be selectively aligned with only a single bundle 23a of the optical fibers shown in FIG. 4. The control sub-unit 45 will control movement of the mask 42 so that each bundle 23, in turn, is illuminated. This will cause the illumination optical energy to be emitted from one of the columns 22 shown in FIG. 5, and as the mask 42 moves, different ones of the columns 22 of optical fibers will illuminate the target tissue.

The detection sub-unit 50 may comprise a re-imaging device 52, a collection filter wheel 54, a spectrograph 56 and a CCD camera 58. The collection filter wheel 54 is optically coupled to the spectrograph and holds a plurality of filters (not shown) for filtering the collected optical energy before it is sent into the spectrograph 56. Exemplary filters for multiple spectral measurements are listed in FIG. 6. Filtering can be used to reduce artifacts due to reflected excitation from the target tissue. When attempting to measure fluorescent emissions from the target tissue, which have a very low amplitude, a reduction in the reflected excitation energy or light amount is quite helpful. The insertion of filters, however, can change the light path between the optical fibers and the spectrograph entrance slit.

The collected optical energy, which has traveled through, for example, optical fibers to the detection sub-unit, is re-imaged at the entrance slit of the spectrograph 56 by a re-imaging device 52, such as, for example, an FC-446-30 from Roper Scientific-Acton Research (Action Mass.), which does this without introducing chromatic aberrations and astigmatism. Such a re-imaging device may include a spacer (not shown) which allows insertion of a motorized collection filter wheel, such as, for example, an FA-448-2 filter wheel also from Roper Scientific-Acton Research. The re-imaging device permits simple, straightforward insertion of the filter wheel.

The collection pathway 60, which may be, for example, a coherent bundle of optical fibers 60, which carries optical energy collected from the target tissue, is placed at the entrance of the re-imaging assembly. At any given time, the illumination pathway 44, which may be, for example, optical fibers, will only illuminate a column of positions on the target tissue. Thus, optical energy collected into the collection pathway 60 will only be from approximately the same column of positions on the target tissue. The result is that, at any given time, the optical energy entering the spectrograph 56 from the return optical fibers 60, will be arranged in a virtual vertical slit.

The spectrograph 56 takes the vertical slit of returned optical energy, and resolves the optical energy into different wavelengths by separating the energy or light in the horizontal direction. The result is an energy or light pattern having two dimensions, wherein the vertical dimension corresponds to different positions on the target tissue, and wherein the horizontal dimension corresponds to different wavelengths. The two dimensional energy or light pattern is then recorded on a camera, for example, a CCD camera 58.

The spectrograph may be, for example, a customized, approximately 300 mm focal length, f#4, Czerny-Turner configuration spectrograph, such as the SpectraPro SP-306I, manufactured by Roper Scientific-Acton Research (Acton Mass.). According to one embodiment of the invention, the grating of the spectrograph has the following specifications:
Grooves/mm: 100 nm/mm
Dispersion: 32 nm/mm
Blaze angle: 1 17'
Field of view: 365 nm The camera may be a CCD camera, for example, a thermoelectrically cooled CCD camera, such as the NTE/CCD-512SB manufactured by Roper Scientific-Princeton Instruments (Princeton, N.J.) with a SITE 512×512, square format, approximately 24 in pixel, back illuminated detector, along with the ST-133 high speed DMA serial interface controller. The A/D converter in the controller allows a 1.0 MHZ A/D scan rate. However, other types of cameras commonly known to those skilled in the art may be used.

In one embodiment, the control unit 45 is a software/hardware package comprised of an instrument control section, a graphical user interface, and data storage capabilities. For example, a compact PC with adequate ports and bays to accommodate the requisite interfaces and PCI cards may be used for this purpose. The control unit 45 provides control over actuation of the illumination and collection filter wheels 38, 54, the safety shutter 36, the camera shutter (not shown), the camera controller (not shown), data conversion and transfer to the PC (not shown), the spectrograph grating adjust motor (not shown), the imaging camera 68 and corresponding illumination source 32 and the stepper motor (not shown) for the motorized mask. Control is provided according to a schedule template that can be modified by the user.

In addition, the software may provide graphical feedback to the user showing images (video and spectroscopy) that are used to make real time determinations of measurement adequacy. The program stores the measured data, which may include tissue particulars, measurement particulars and/or images. The measured data for each tissue can then be downloaded and stored in a portable recording medium (not shown) such as a magnetic or optical disk.

The above described embodiment, which includes a spectrograph for spectrally resolving the light returning from the target tissue, is but one way to accomplish the spectral resolution. In other embodiments of the invention, other devices such as prisms or transmissive gratings, for example, could be utilized to spectrally resolve light returning from a location on a target tissue into different wavelengths. Yet, even further, other devices known to those of ordinary skill in the art could be utilized. For purposes of discussion and example only, a spectrograph will be discussed as the spectrally resolution device.

In addition, in some embodiments of the device, it may prove more advantageous to take measurements at a plurality of locations on a target tissue to measure a single narrow wavelength band of returned light during a first measurement cycle. Another measurement cycle could then be conducted at the same locations on the target tissue for one or more different wavelength bands.

Furthermore, in the embodiment described above, the illumination light was conveyed to the target tissue such that it sequentially illuminated several different columns of positions on the target tissue. In other embodiments of the invention, the illuminated positions on the target tissue need not be illuminated in a column arrangement. In fact, it some embodiments of the invention, it may be advantageous to arrange the optical fibers such that each sequential illumination and measurement cycle measures the characteristics of widely separated locations across the target tissue. Once all measurements have been taken, the measurement results could be re-combined by the device operating software to present an image indicative of the target tissue characteristics. A device configured in this manner would greatly reduce the occurrence of cross-talk between illuminated positions.

The systems, methods and apparatus according to the present invention use the hyperspectral imaging approach discussed by J. Marno in "Hyperspectral imager will view many colors of earth," Laser Focus World, August 1996, p. 85. This involves measuring intensities of optical energy emitted from tissue at high spectral and spatial resolution.

Systems, methods and apparatuses embodying the present invention should be designed to ensure that, as between measurement speed, spectral resolution, and spatial resolution, the most important characteristics are measured with the highest resolution in the shortest possible time period.

In order to obtain spectra free of environmental or system artifacts, one approach would be to calibrate the system embodied by the present invention. The calibration procedures are as follows: (1) provide an absolute scale to the intensity measurements at each wavelength; (2) provide an absolute wavelength scale; (3) correct for fluctuations in lamp intensity and spectral shifts; (4) correct for spectrograph/grating performance limitations due to stray light; (5) correct for background light; (6) correct for noise; and/or (7) correct for variance and temporal changes in optical properties, spectral transmittance, reflectance lenses and fibers. Providing an absolute scale to the intensity measurements at each wavelength calibrates the detection elements of the system and provides an absolute scale to the intensity measurements. This will also allow identification of performance variations in the source and detection system.

With respect to noise, there exists categories of potential noise that might typically occur with measurements comes from several possible sources. Without limitation, they include shot noise, instrument noise, clinical noise, and physiological noise.

Shot noise is equal to $\sqrt{I}$ and refers to the inherent natural variation of the incident photon flux. Photoelectrons collected by a CCD exhibit a Poisson distribution which have this square root relationship between signal and noise.

Instrument noise includes several individual noise types classified according to their sources such as CCD noise including the read noise and dark noise and dependent on the A/D transfer rates and the temperature of the CCD, respectively. Additional sources of instrument noise include, without limitation, variability in lamp intensity, variability in the transmittance of optical components such as fibers filters and lenses, and variability in the transmittance of fibers due to fiber bending.

Clinical noise is the noise that arises from the clinical measurement procedure such as the distance/angle between the target tissue and the device, presence of blood and mucus as well as patient/device movement.

Physiological noise is the non-diagnostic natural variability of the biochemical and morphological properties of tissue. The physiological noise can be one of the most challenging to address. To alleviate this noise source is to normalize or compare the intensities measured at any tissue site with the intensity from a 'clinically normal' site. The normal site is identified using simple tests such as the maximum or minimum intensity or intensity ratio.

The signal to noise ratio of a measuring device is simply $$SNR = \frac{I}{\sigma(I)}$$

where I is the measured signal intensity, and σ(I) is the noise or standard deviation of the measured intensity. We have taken steps to ensure that signal corruption in our device from the cumulative effects of these noise sources is reduced or eliminated. The specific steps include:

A. Obtaining a high enough signal intensity such that the noise in the measurement in dominated by the shot noise. The shot noise is an inherent property of the CCD response and given that it increases as $\sqrt{I}$ with increase in I, its proportion as a percentage of I decreases with increase in I. At a high value of I the contribution of shot noise is negligible. We have attempted, as listed below, to reduce other noise sources to a value below that of shot noise i.e. the instrument operates in the shot noise dominated regime;

B. Keeping the temperature and the A/D transfer rate at the lowest optimum, thus minimizing read and dark noise;

C. Measuring the lamp power simultaneously with the tissue measurement. The tissue measurement is then normalized by this measured lamp intensity. This removes/corrects for the noise in the measured intensity due to variability in lamp intensity and variability in the transmittance of optical components such as fibers, filters and lenses;

D. Using ratios of intensities at different wavelengths rather than straight intensities since this method internally corrects for changes in transmittance and also corrects for variations in light coupling due to changes in the way the target tissue is oriented with respect to the light beam. This method is limited to transmittance changes that do not vary across the spectrum; and E. Optimizing the clinical procedure to minimize the clinical noise. This includes an adequate tissue cleaning procedure and keeping the device weight and shape conducive to holding it without significant motion artifact.

Next, the horizontal dimension of the CCD, measured in pixel number is used to mark the wavelength of the measured intensity. A wavelength number is assigned to each pixel. Establishing these absolute scales contribute to the calibration of the present invention.

Calibration standards may include those commonly used by ones skilled in the art. For example, spectral irradiance standards may utilize a NIST traceable Quartz Tungsten halogen lamp for wavelengths greater than approximately 400 nm. For wavelengths less than approximately 400 nm, a NIST traceable Deuterium lamp may be used. Wavelength calibration standards may include, without limitation, mercury lamps and NRCC traceable Erbium Oxide lamps. With respect to the former, these lamps have narrow, discrete spectral lines over UV and visible wavelengths that provide a metric for wavelength calibration. For example, for diffuse reflectance standards, a NIST traceable Spectralon™ from LabSphere, Inc. (North Sutton, N.H.) may be utilized. The reflectance of these standards is highly lambertian over their spectral range. They also have a spectrally flat reflectance profile, i.e. the percent of radiation reflected at each wavelength (within the usable wavelength range) is constant. For diffuse fluorescence standards, ones such as those produced by LabSphere, Inc. may be used. These standards are also made of Spectralon™ and one further embedded with inorganic fluorophores that provide a highly stable, reproducible fluorescence.

In addition to absolute scale, calibration must correct for variances and potential external and/or internal interferences. Fluctuations in lamp intensity and spectral shifts may need to be corrected for, since arc lamps such as the ones used according to certain embodiments of the present invention are known to display fluctuations in energy output based on lamp life, duration of use and ambient conditions. Since the present invention determines tissue characteristics based on intensity measurements, such variations should be taken into consideration and accounted for by appropriate calibration. Similarly, it is helpful to correct for stray light that may result from the inability of a monochromator grating to perfectly separate light of different wavelengths. Grating efficiency, inadequate baffling and the use of short optical path lengths needed to make a compact instrument all contribute to stray light and therefore, should also be accounted for by appropriate calibration. In addition to stray light, background light may also be a factor to consider. Light leakage into the system that results in erroneously higher intensities must be measured and subtracted.

Finally, in addition to absolute scales and internal and/or external light factors, calibration of the present invention may also include accounting for dark noise and variance and temporal changes in optical properties, spectral transmittance, reflectance of lenses and fibers. With respect to dark noise, this issue primarily arises as a result of thermal, non-thermal and readout noise characteristics of the CCD detector. Although embodiments of the invention use a PET cooled detector, the noise can be significant and needs to be subtracted out. With respect to factors effecting optical properties, spectral transmittance, reflectance of lenses and fibers, each spot/location of light projected on the tissue varies in intensity. This variance may be due to the axial position of the spot and small differences in individual fibers and mask apertures. The intensities of the spots/locations may change with time due to changes in alignment and component degradation.

The present invention utilizes at least one calibration during its operation. One type of calibration is before the initial operation of a device embodying the invention or when the device needs maintenance and/or repair. This will be referred to as pre-operative calibration. Pre-operative calibration may comprise an absolute calibration protocol and a wavelength protocol.

Figure 21:
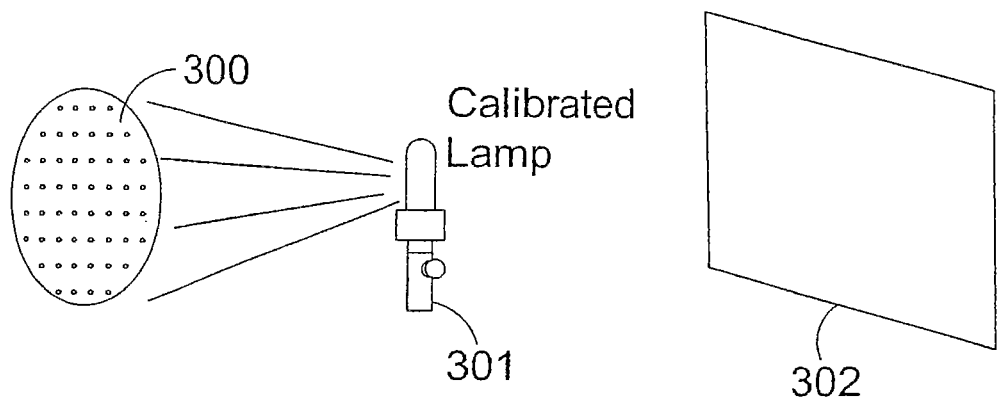
FIG. 21 is a schematic drawing of a setup for absolute calibration of a system embodying the invention.

Absolute calibration applies irradiance standards to establish performance benchmarks and to provide an absolute scale to the intensities measured. The irradiance standards allow the coupling of known intensity levels into fibers or apertures. A schematic diagram of a setup for performing calibration is shown in FIG. 21, where 300 designates an aperture mask, 301 designates a light source, and 302 designates a black absorbing material. The aperture mask 300 shown may be replaced with an excitation fiber bundle, where the light is coupled into fibers at one end of the bundle. The light emerging from the other side of these apertures or the other end of the fiber bundle can be imaged by the detection system and the measured intensity calibrated against the known intensity to arrive at a correction factor which will be further taught below.

To calibrate wavelengths, wavelength calibrations are used. The light source 301, such as a calibrated mercury arc lamp, is positioned between a focusing lens (not shown) and the mask 300 in FIG. 21 while the arc lamp is off or the safety shutter is closed to ensure only illumination from the mercury lamp enters the system. A reflectance target is held before the sight tube, taking care to seal off and prevent room light from entering the system. The columns of illuminated spots are spectrally resolved on the CCD. The known natural peaks of the mercury spectrum, when the embodiment is a mercury lamp, are captured and are used for calculating a wavelength scale for each image. A set of eight software driven measurements that account for each of the eight column positions on the target, are made as show in the table of FIG. 22 using the instrument settings indicated for each measurement.

In addition to, or alternatively, the present invention can be calibrated prior to each measurement. This calibration will be referred to as "operative calibration". This calibration corrects for both short-term system, intermediate and long-term fluctuations, such as lamp degradation, for example. The method that performs this calibration may be embodied in a software program using the instrument settings listed in the tables of FIGS. 23 and 24.

The operative calibration comprises a reflectance calibration, a fluorescence calibration, and a background and dark noise calibration. The reflectance calibration may, according to certain embodiments, comprise of positioning the Spectralon™ diffuse reflectance target before the sight tube so as to exclude room light from the system. A series of measurements given the instrument settings listed in the table of FIG. 23 are made. During a fluorescence calibration, the Spectralon™ (or other comparable) fluorescence target is positioned before the sight tube taking care to exclude room light or other superfluous light from the system. A series of measurements given the instrument settings listed in the table of FIG. 24 are made according to one embodiment of the present invention. According to this embodiment, the measurements may be made in sets of three where each set may use a different excitation and emission wavelength selected by choosing a different filter set.

Finally, background and dark noise calibration may be incorporated into the fluorescence and reflectance and calibrations above as well as into each subject target tissue/area measurement. According to certain embodiments, the first measurement of each sequence of 8+1 measurements in the tables of FIGS. 23 and 24 is a background measurement where the safety shutter is held closed. This measurement accounts for the error that may be caused due to room light and/or other electronic noise sources that may result in the CCD reading an intensity signal. This type of result may be defined as background noise and is subtracted from each of the calibration and tissue measurements.

The data collected from pre-operative and/or operative calibrations are used to calculate a set of correction factors for absolute calibration as follows:

$$C(f,\lambda) = T(f,\lambda)/M(f,\lambda)$$

where f is the position/spot number or aperture location in the target area and $\lambda$ is the wavelength (~400-700 nm). $T(f, \lambda)$ is the true intensity from the standard coupled into the aperture at least one wavelength, and $M(f, \lambda)$ is the intensity measured by the system from that aperture at that at least one wavelength. All spectra acquired with the same detection system can then be multiplied point-for-point by these correction factors in order to eliminate effects of the non-uniform response (spectral and spatial) of the detection system.

In calibrating wavelengths, the measured spectrum of a mercury light source contains sharp peaks which correspond to the spectral lines of the source. The wavelength of each corresponding spectral line can be assigned to the pixel number along the horizontal axis of the CCD for each position of the peak. With two or more peaks present in the spectrum, a linear interpolation is then used to determine the wavelength values for all the pixels.

For operative calibration, the protocol comprises a reflectance intensity calibration, a fluorescence intensity calibration, and a stray light or other superfluous light calibration. Intensity calibration measurements for reflectance spectra are performed by normalizing the spectrum measured from each spot on a tissue with the spectrum measured from the same spot on the reflectance calibration target. This is done after subtracting the background light from each measurement. This procedure eliminates any error from spot-to-spot variations in excitation intensity and can be expressed as follows:

$$R(f,\lambda) = \{[R_S(f,\lambda) - B_S(f,\lambda)]/[R_R(f,\lambda) - B_R(f,\lambda)]\} * T_R(f,\lambda),$$

where $R_S(f, \lambda)$ is the reflected intensity spectrum measured from the subject target area and $R_R(f, \lambda)$ is the reflected intensity spectrum measured from a reference whose true reflectance $T_R(f, \lambda)$ is known. This true reflectance is provided by a diffuse reflectance standard whose reflectance is substantially constant for all wavelengths used in the system taught by the present invention.

$B_S(f, \lambda)$ is the background measurement corresponding to the tissue reflectance measurement, e.g. tissue background measurement taken using the same instrument settings as the tissue measurement, but with the safety shutter closed. $B_R(f, \lambda)$ is the background measurement corresponding to the reference measurement. With these measurements, a meaningful estimate of tissue reflectance $R(f, \lambda)$ may be obtained.

For fluorescence spectra, intensity calibration involves normalizing the fluorescence spectrum from each location on the target area by the fluorescence intensity from the same location when measuring on the fluorescence calibration target. Then, either the integral or the peak of each position's intensity spectrum may be used to normalize spectrum using the following formula:

$$F(f,\lambda) = [F_S(f,\lambda) - B_S(f,\lambda)] / [F_R(f,v) - B_R(f,\lambda)]$$

where $F_S(f, \lambda)$ is the fluorescence spectrum measured on subject target area and $B_S(f, \lambda)$ is the corresponding background measurement taken using the same instrument settings as the subject target area measurement but with the safety shutter closed, $F_R(f, \lambda)$ is the measurement on the fluorescence reflectance standard, $B_R(f, \lambda)$ is the corresponding background measurement, and $F(f, \lambda)$ is the corrected fluorescence spectrum.

With respect to stray light or superfluous light calibration, correcting each fluorescence spectrum for the stray light output of the excitation monochromator involves subtracting the stray light spectrum reflected from the tissue from the measured fluorescence spectrum of the tissue. This correction employs the principle that the absolute reflectance (as a function of wavelength) is independent of the spectrum used for illumination. This principle can be expressed as an extension of the immediately preceding equation as follows:

$$\{R_S[I_1(f,\lambda)] - B_S[I_1(f,\lambda)]\} / \{R_R[I_1(f,\lambda)] - B_R[I_1(f,\lambda)]\} = \{R_S[I_2(f,\lambda)]\} / \{R_R[I_2(f,\lambda)] - B_R[I_2(f,\lambda)]\}.$$

Here, $I_1$ is the standard, broadband output of the illumination system used to measure reflectance of tissue, for example, and $I_2$ is the stray/superfluous light of the illumination system that accompanies the monochromatic excitation used for tissue fluorescence measurements. Thus, tissue calibration may be achieved by normalizing this procedure with the standard reflectance. The result is a calibration factor, as follows:

$$\{R_S[I_1(f,\lambda)] - B_S[I_1(f,\lambda)]\} / \{R_R[I_1(f,\lambda)] - B_R[I_1(f,\lambda)]\}$$

which when multiplied by the stray/superfluous light spectrum measured on the standard from supposedly monochromatic excitation gives the stray/superfluous light inadvertently measured along with tissue fluorescence. This is illustrated by rearranging the equation such that:

$$R_S[I_2(f,\lambda)] = (\{R_S[I_1(f,\lambda)] - B_S[I_1(f,\lambda)]\} / \{R_R[I_1(f,\lambda)] - B_R[I_1(f,\lambda)]\}) * \{R_R[I_2(f,\lambda)] - B_R[I_2(f,\lambda)]\}.$$

$R_R[I_2(f, \lambda)]$ and the corresponding $B_R[I_2(f, \lambda)]$ are measured in a similar way as discussed in the previous section for intensity calibration of fluorescence spectra. The reflectance standard is illuminated with monochromatic light (and associated stray light), and the measurement focuses on wavelengths at which stray light is present (i.e. longer than the excitation wavelength) rather than the excitation bandwidth. $R_R[I_2(f, \lambda)]$ is then subtracted from the measured fluorescence spectrum.

After the present invention has been calibrated, the tube 72 of the tissue interface unit 70 may be first inserted into the patient's vagina so that the end of the tube is immediately adjacent, or covering the patient's cervix. The cervix is then illuminated by the illumination source 76. Collected optical energy transmitted and/or reflected from the tissue is directed to the imaging device 78, which, in this embodiment, is located in the tissue interface unit 70. The imaging device 78 sends a video signal that is viewed with a computer or video monitor (not shown). Thus, the imaging device 78 provides the user with a view of the patient's cervix, which assists the physician in properly aligning and situating the tube 72 with respect to the patient's cervix. The imaging device 78 may also be used to capture still images of the cervix, which may be digitally stored and used for later data analysis.

The tube 72 is appropriately placed such that a good view of the subject target area can be seen through the imaging device 78, the tissue interface unit is fixed in place relative to the subject target area. At this point, a still picture of the subject target area may be taken with the imaging device. The illumination device 76 is then turned off, and the spectroscopic measurements are started. As described above, a series of measurement cycles would be conducted. During each measurement cycle, a column of positions on the subject target area would be illuminated, and the light returning from the subject target area would be detected by the detection sub-unit. During each measurement cycle, the spectrograph would spectrally resolve the column of positions into a two-dimensional image that is captured by the camera 58. Each two dimensional image would be arranged such that one axis is indicative tissue position, and the other perpendicular axis would be indicative of wavelength. The two dimensional images recorded during the measurement cycles would then be recorded and analyzed by the device operating software in the control sub-unit 45.

Figure 7A:
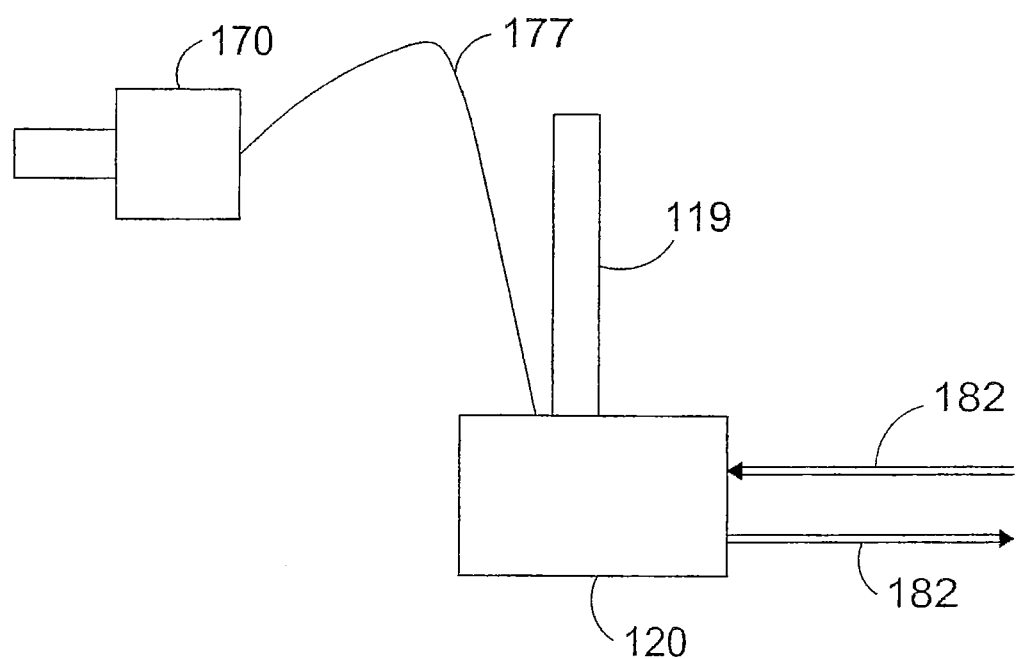
FIGS. 7A and 7B are schematic drawings of a system for determining tissue characteristics according to another embodiment of the invention.
Figure 7B:
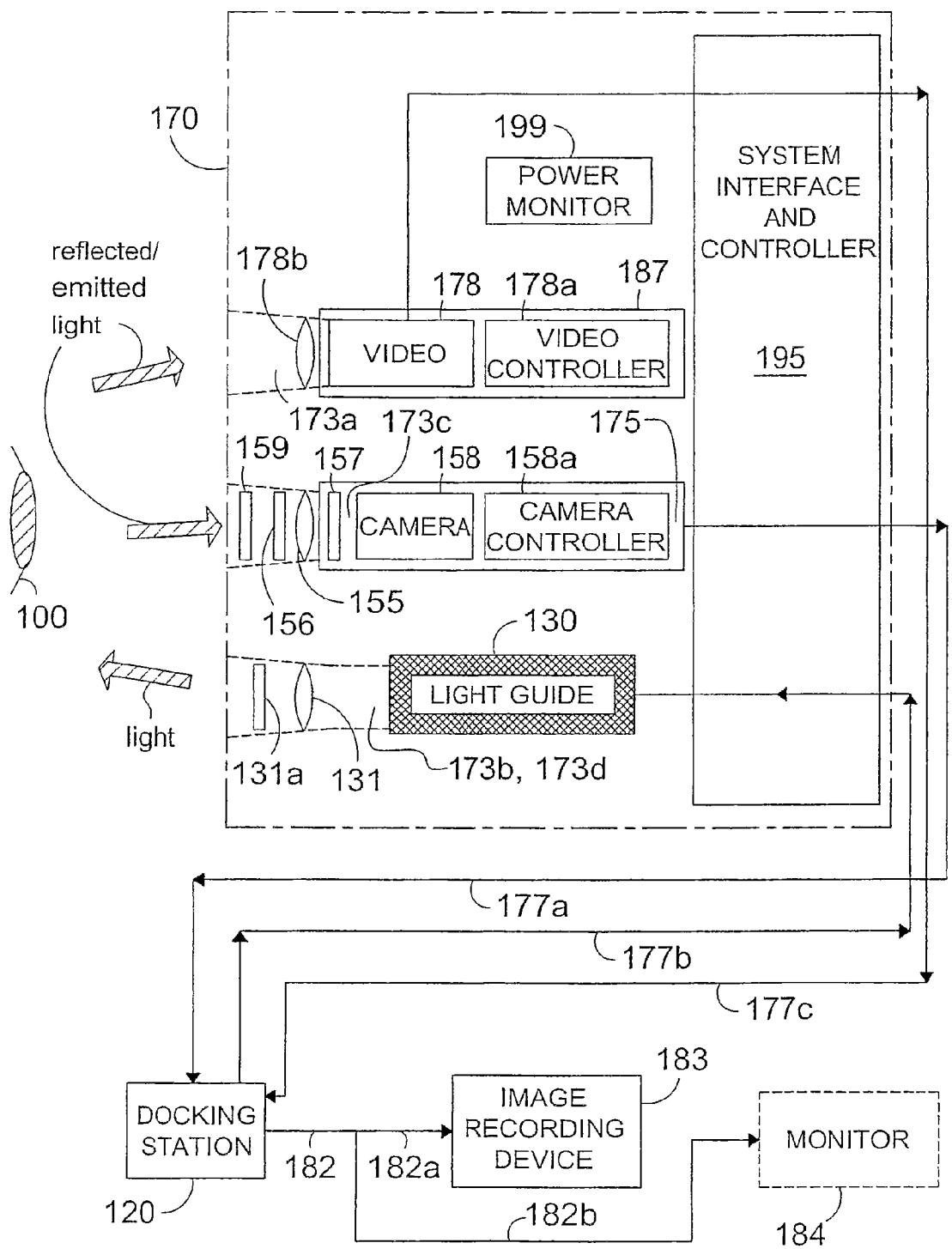

FIGS. 7A and 7B are schematic drawings of a system for determining tissue characteristics according to another embodiment of the invention. The system 110 includes a tissue interface unit 170, which may be configured as a handheld probe-type unit, and a docking unit 120. The tissue interface unit 170 and the docking unit 120 communicate with each other via communication pathway 177, which may comprise one or more optical fibers or other type of signal cable.

The docking unit 120 may include a stand or cradle 119 for docking or holding the tissue interface unit 170 when not in use. The docking unit 120 may also include one or more pathways 182 for outputting or receiving signals to or from additional system components, such as a image recording device, such as a VCR or other type image recording device 183 or monitor 184, such as a color TV monitor (shown in FIG. 7B).

Figure 8A:
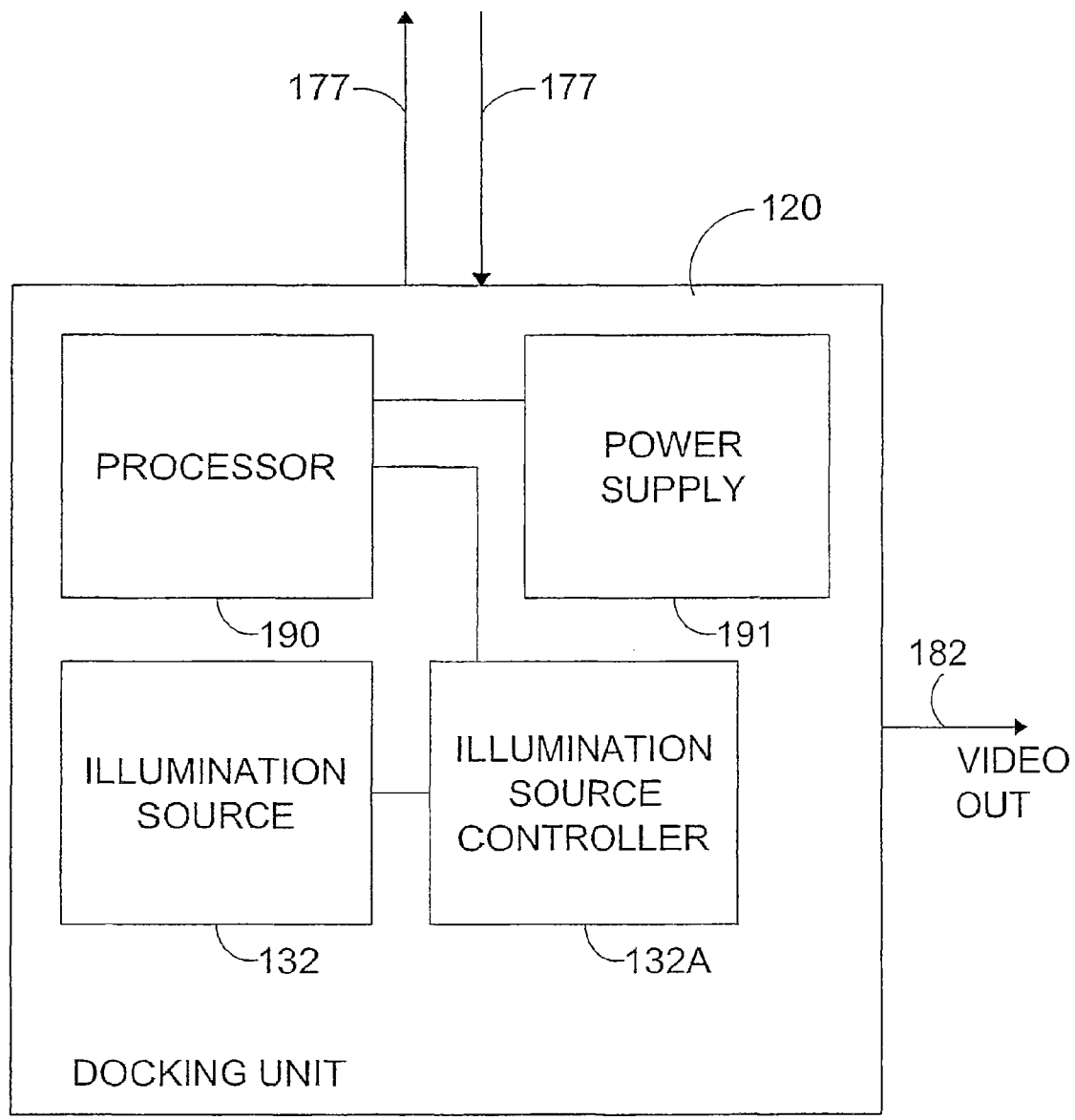
FIG. 8A is a schematic drawing of a docking unit of a system for determining tissue characteristics according to another embodiment of the invention.

As shown in FIG. 8A, the docking unit 120 may further include a processor 190, a power supply 191, an illumination source 132 and an illumination source controller 132a. The docking unit 120 may also include a light guide (not shown), such as a liquid light guide that guides optical energy from the illumination source, for example, into an optical fiber or other type cable to be delivered to the tissue interface unit 170.

As shown in FIG. 7B, the tissue interface unit 170 includes illumination pathways 173b, 173d, which may comprise a single or multiple pathways. These pathways 173b, 173d may include one or more light guides 130 that receive optical energy from the illumination source 132 disposed in the docking unit via communication pathway 177b. The tissue interface unit may also include an illumination lens assembly 131 and an illumination aperture/filter 131a that provides for selective wavelength filtering and a shutter function, also shown in FIG. 7B.

The tissue interface unit 170 further includes a collection pathway 173c, which guides optical energy reflected and/or emitted by a subject tissue to a device for making spectroscopic measurements 175. The device for making spectroscopic measurements 175 may include a diffraction grating 157, a camera 158, and camera controller 158a. The camera and camera controller may be, for example, a CCD camera controlled by a CCD camera circuit card assembly. The spectroscopic measurements may be sent to the processor 190 disposed within the docking unit 120 via communication pathway 177a for processing. According to one embodiment of the invention, the system is capable of detecting reflectance information between approximately 360 nm and 660 nm at a resolution and fluorescence information at 2 or 3 wavelength bands. According to various embodiments, the resolution and wavelength bands can range from 2 nm to 30 nm. According to one embodiment, the resolution is at 20 nm as are the wavelength bands. Each frame of data is transferred from the tissue interface unit to the docking unit for processing.

The collection pathway 173c may include a shutter 156 that blocks out illumination optical energy when spectroscopic measurements are not being made, a filter 159 that provides for selective filtering of wavelengths not of interest, and a collection lens assembly 155.

The tissue interface unit 170 may further include an imaging pathway 173a that guides reflected optical energy to an imaging device 187. The image pathway 173a may also include a lens assembly 178b. The imaging device 187 comprises, for example, camera 178 and camera controller 178a. The camera and camera controller may be, for example, a video camera and video camera controller, or any similar type image recording device. The video imaging channel according to one embodiment may have a resolution of 300 TV lines (NTSC analog output for video recording and display) with fixed magnification and focus, a field of view of approximately 25 mm, and a depth of field of approximately +/−5 mm. The imaging device 187 allows a user to view the subject tissue in order to position the tissue interface unit 170 with respect to the subject tissue. The tissue interface unit 170 may include a monitor, or may communicate with a separate monitoring device to permit viewing of the tissue by a user. Additionally, the tissue interface unit 170 may include a user interface (not shown) that provides for entry of patient information, for example.

Figure 8B:
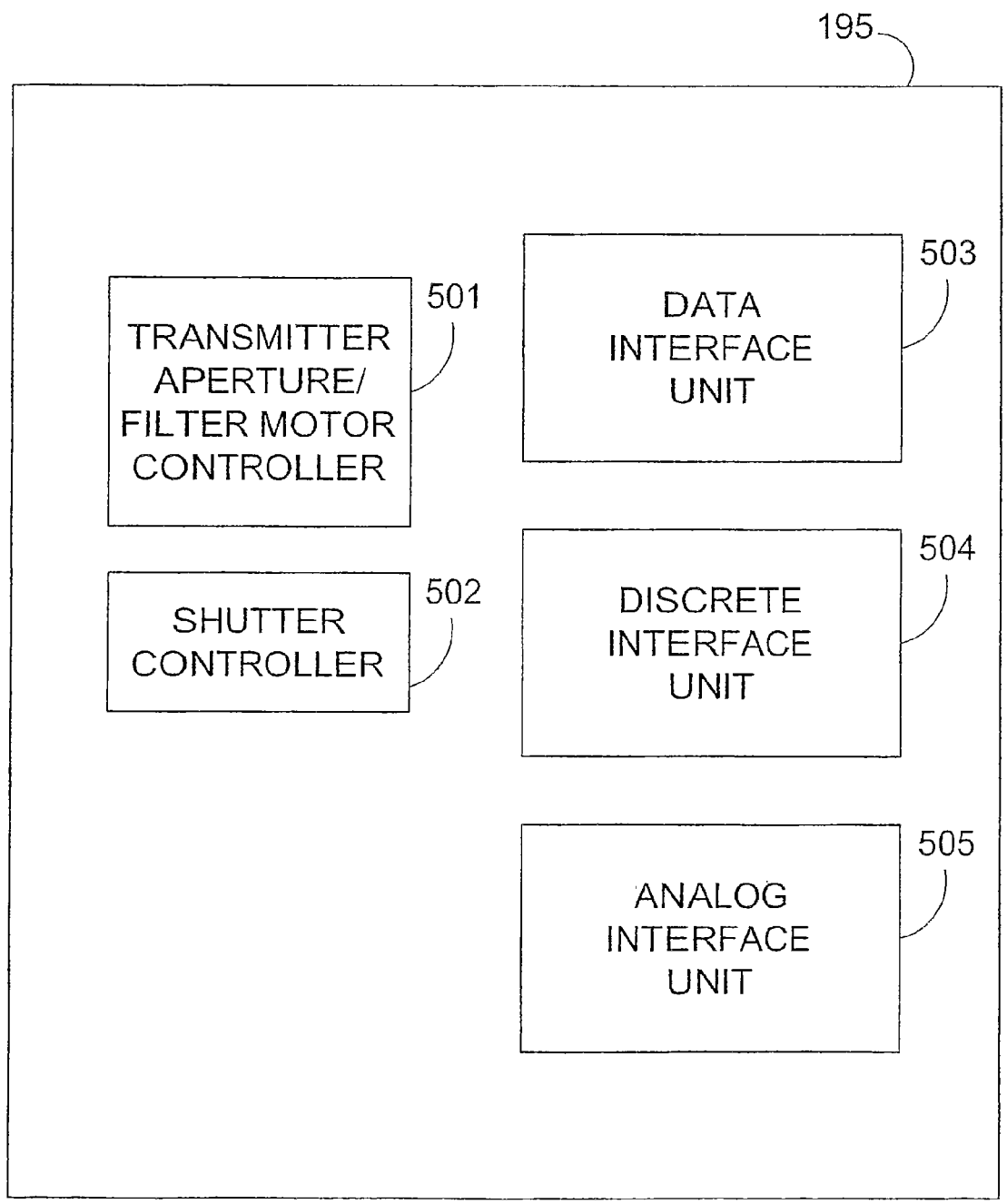
FIG. 8B is a schematic drawing of a system interface and controller of a system for determining tissue characteristics according to another embodiment of the invention.

The tissue interface unit further includes a power monitor 199 and a system interface and controller 195, as shown in FIG. 7B. As shown in FIG. 8B, according to one embodiment of the invention, the system interface and controller 195 includes a data interface unit 503 that controls the exchange of data signals between the tissue interface unit 170 and the docking unit 120. The system interface and controller 195 may further include a discrete interface unit 504 that controls the system's respective power and switches, and an analog interface unit 505 that controls the systems interface with an external image recording device 183. The system interface and controller 195 may also include a shutter controller 502 that controls operation of shutter 159 and an illumination aperture/filter controller 501 that controls operation of the motor of the illumination filter.

Figure 11:
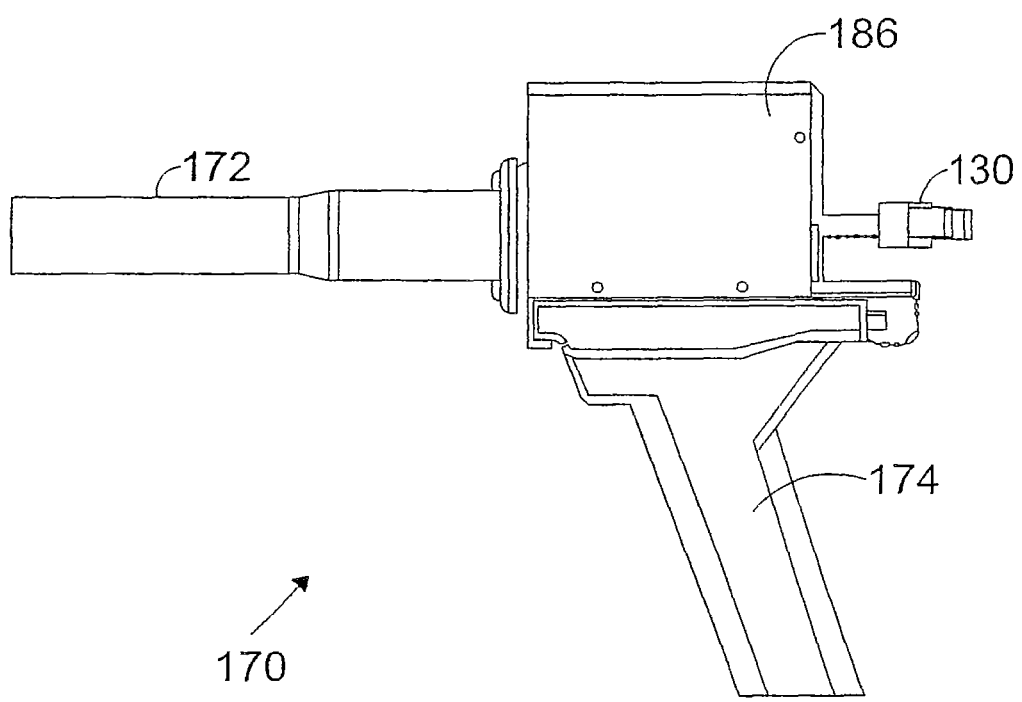
FIG. 11 is a side view of a tissue interface unit of a system for determining tissue characteristics according to another embodiment of the invention.
Figure 12:
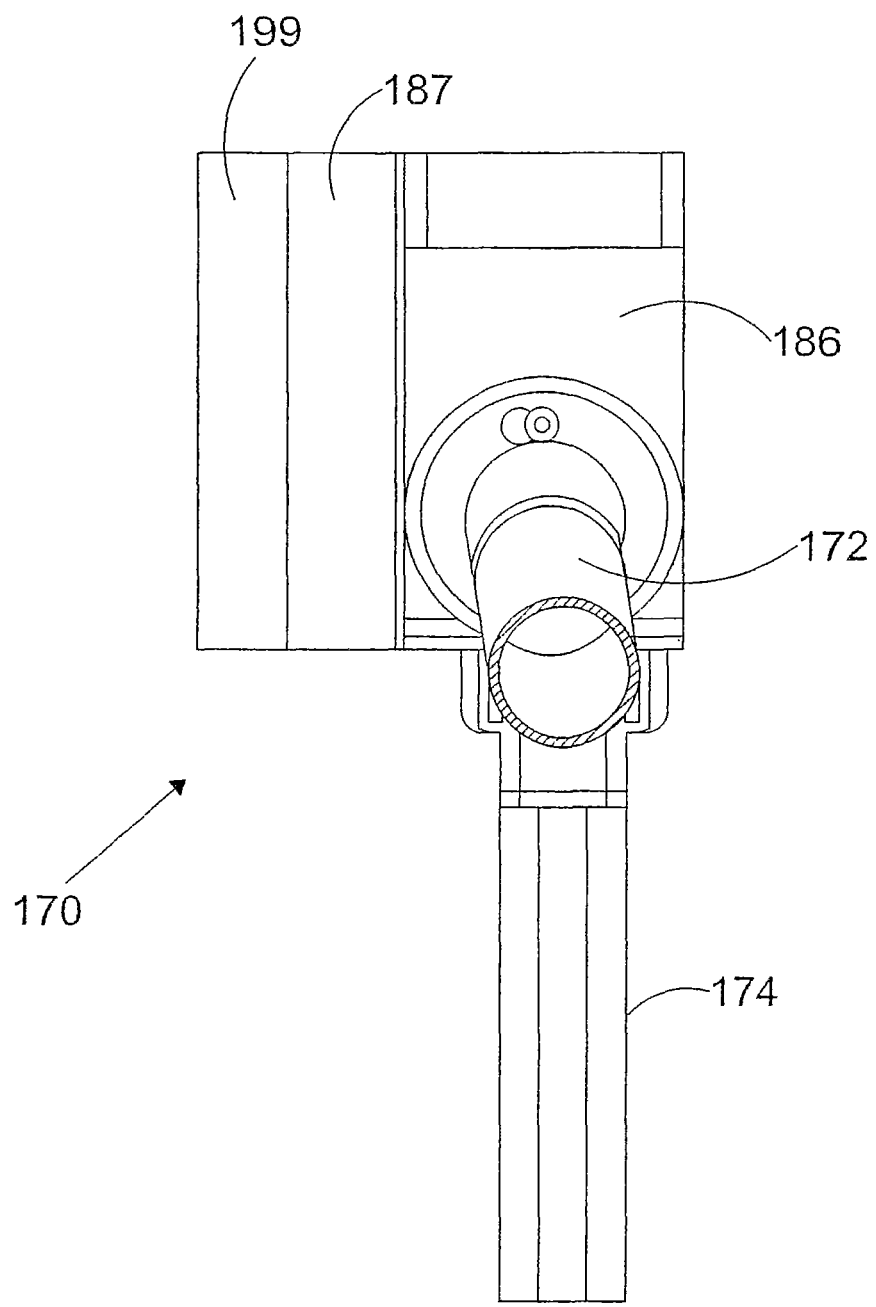
FIG. 12 is a front perspective view of a tissue interface unit of a system for determining tissue characteristics according to another embodiment of the invention.

An example of one embodiment of a hand-held tissue interface unit according to the invention is shown in side view in FIG. 11. The tissue interface unit 170 includes housing 186, a handle 174 configured to be graspable by a user, a tube 172 that delivers illumination optical energy to a subject tissue, and optical energy reflected and/or emitted by the subject tissue to the viewing device and/or the spectroscopic measurement device, and a liquid light guide 130 that guides optical energy received from a docking unit 120 into the tube 172. The tube 172 may be removable, as discussed below, and may be disposable. As shown in FIG. 12, the tissue interface unit 170 may also include a heat sink 199 that maintains the tissue interface unit within an acceptable temperature range.

Figure 9:
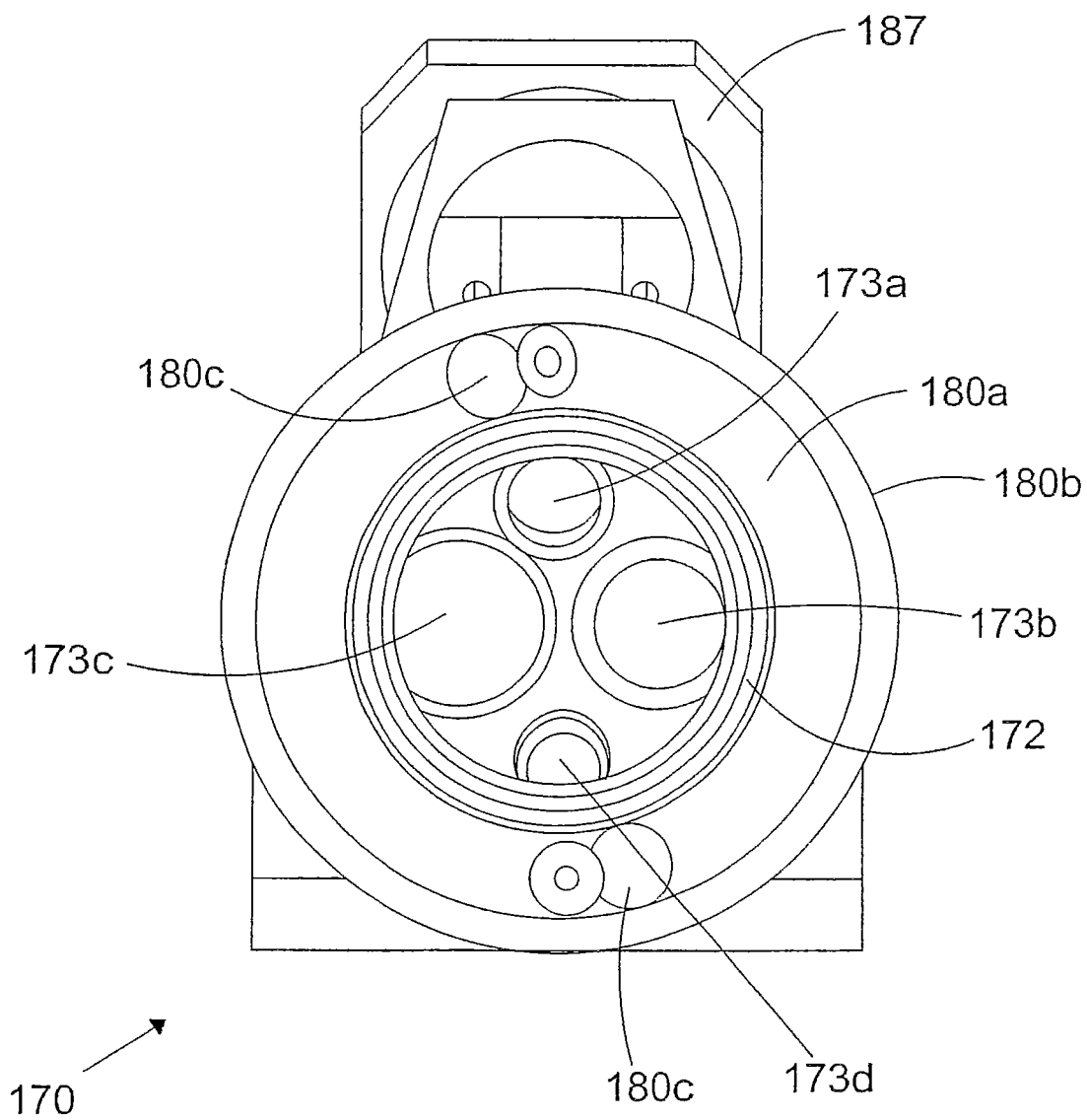
FIG. 9 is a front view of a tissue interface unit of a system for determining tissue characteristics according to another embodiment of the invention.
Figure 10:
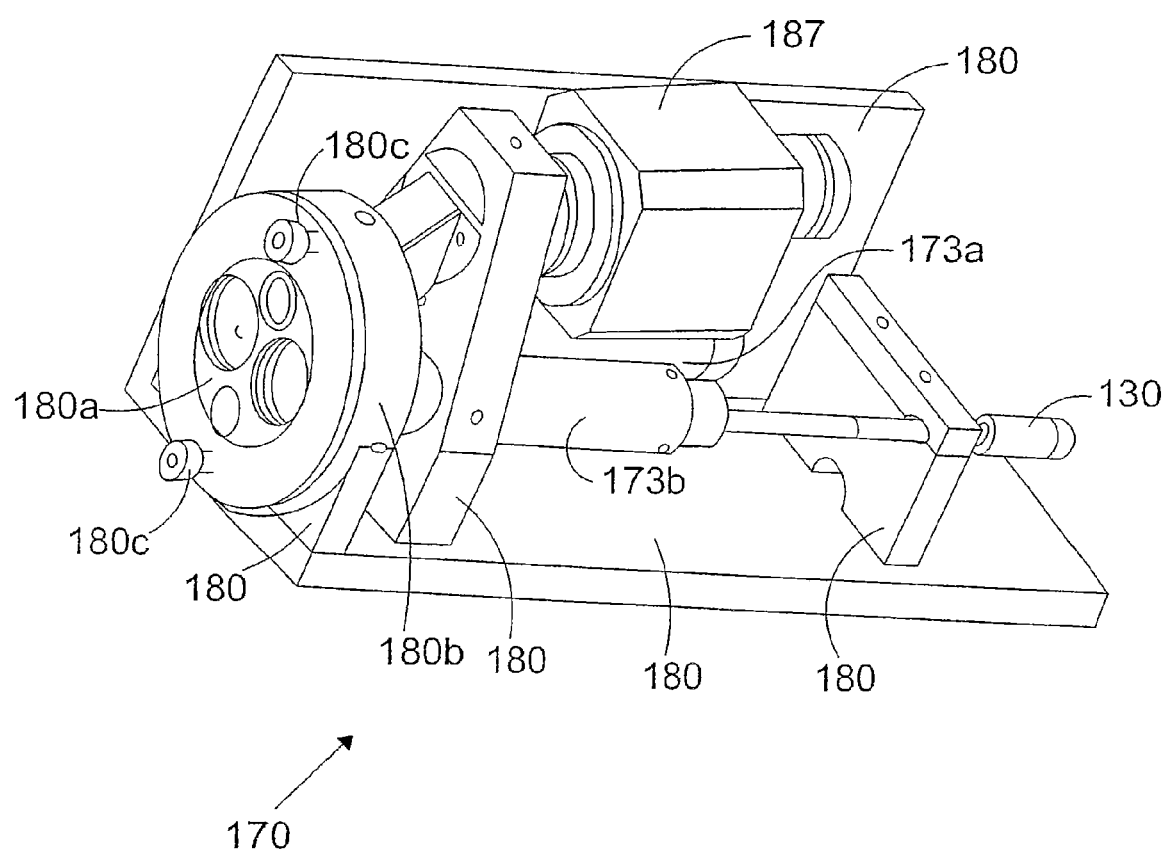
FIG. 10 is a side perspective view of the tissue interface unit of a system for determining tissue characteristics according to another embodiment of the invention.

FIG. 9 is a front view of a tissue interface unit according to the invention without outer casing 186, and handle 174. FIG. 10 is a side perspective view of the tissue interface unit of FIG. 9 without outer casing 186 and tube 172. As shown in FIGS. 9 and 10, the tube 172 connects to the base structure 180 via a plate 180b. The plate 180b has an endface 180a. The endface 180a includes openings for illumination pathways 173b, 173d, collection pathway 173c and imaging pathway 173a. These pathways share tube 172 in such a way that no interference occurs between pathways. Tube 172 may be attached to endface 180a by some type of attachment means 180c, as shown in FIG. 9.

In an embodiment of the invention configured to detect tissue characteristics of a patient's cervix, the tube 172 of the tissue interface unit 170 may be first inserted into the patient's vagina so that the end of the tube is immediately adjacent, circumscribing or covering the patient's cervix. The cervix is then illuminated by the illumination source 132 via illumination pathway 173d. Collected optical energy transmitted and/or reflected from the tissue is directed to the imaging device 187, which is located in the tissue interface unit 170. The imaging device 187 sends a video signal that is viewed with a computer or video monitor. Thus, the imaging device 187 provides the user with a view of the patient's cervix, which assists the physician in properly aligning and situating the tube 172 with respect to the patient's cervix. The imaging device 187 may also be used to capture still images of the cervix, which may be digitally stored and used for later data analysis.

Once the tube 172 is appropriately placed such that a good view of the cervix can be seen through the imaging device 187, the tissue interface unit would be fixed with respect to the patient's cervix. At this point, a still picture of the cervix may be taken with the imaging device. The image signal is output to the docking unit or directly to a monitor provided within the tissue interface unit, or as a separate component. For example, the image, along with relevant text, could be displayed on a hand-held LCD unit or a LCD unit attached to the tissue interface unit. The spectroscopic measurements are then started. The spectroscopic measurement results are sent to the processor 190 in the docking unit 120 for processing. For example, the results can be utilized to categorize the spectroscopic measurement data, and thus the subject tissue, as "Normal", "Non-Dysplastic", "Low Grade SIL" and "High Grade SIL."

The systems, methods and apparatus of the present invention, may conduct both fluorescence and reflectance spectroscopy using both visible and UV light or any combination thereof. This is generally referred to as multimodal spectroscopy. Cervical cancer, being a form of epithelial dysplasia, provides an ideal target for diagnosis using the epithelium down to the germinative layer, since it undergoes minimum absorption and scattering from non-specific interactions and obtains the largest possible diagnostic information on its biochemical and morphological state. Other areas with similar qualities that may serve as comparable targets for diagnosis include, without limitation, oral cancer and colon cancer.

Fluorescence and reflectance spectra may be made at several locations on the target area by the present invention. Such locations may be equispaced. Obtaining measurements across the entire target area, for example, may allow for differential diagnosis between dysplasia and surrounding tissue depending on the embodiment.

Many investigators have pointed to the large biological variation in the spectroscopic signature of normal tissue. This natural variation is often higher than the variation seen in the spectroscopic signatures going from normal to dysplasia tissue in the same patient, for example. One cannot, therefore, assign an absolute spectral intensity or signature to disease state. Rather, all measurements must be normalized or baselined to "normal" tissue in the same patient, and it is this relative measure or change that has diagnostic relevance. Given our inability to determine "a priori" the location of abnormal and normal tissue with certainty, the logical alternative is to measure substantially the entire target area.

A reflectance measurement is made by measuring the intensity of light returned from the tissue at the same wavelength as that used to irradiate the tissue. Reflectance measures the morphological changes associated with dysplasia progression. Although biochemical changes precede the morphological changes that occur as a result of the former, in reality, varying degrees of morphological change accompany the biochemical changes. Morphological changes appear later in the course of dysplasia progression and are defined as any change in average cell nuclei, cell size, cell appearance, cell arrangement, and the presence of non-native cells. In addition, effects of the host response such as increased perfusion from angiogenesis result in an overall difference in tissue appearance.

The morphological changes add more complexity to the fluorescence measurement by absorbing and scattering both the excitation and fluorescent light, thereby altering the true fluorescence signal. Thus, it is difficult to make a fluorescence measurement that is truly independent of the effects of scattering and absorption. At the same time, both measurements provide information that is partially independent of one another.

In reflectance spectroscopy, the tissue properties of absorption and scattering dictate the amount of radiation measured at the detector. For example, the increased vascularization due to angiogenesis causes increased blood absorption of visible light. Light propagating through and re-emitted from tissue is also strongly affected by light scattering interactions. For example, dysplasia cells have enlarged nuclei and since nuclei have a different refractive index from that of the cell cytoplasm, they serve as efficient light scatters. Thus, dysplasia tissue can display increased light scattering.

While the absorption and scattering properties of tissue correlate quantitatively with disease, by knowing the absorption and scattering at each site on the tissue the corresponding error that these effects produce in the fluorescence yields can also be corrected for. This is the crux of the multimodal spectroscopy approach. In order to reap this advantage, both measurements must be made on the same site at the same time so as to ensure nearly identical conditions.

The use of near UV and UV wavelengths elicits the fluorescence and reflectance response of intrinsic markers shown to be highly indicative of biological and morphological changes caused by pre-dysplastic conditions in tissue. Accordingly, the systems, methods and apparatus according to the invention may be configured to acquire broad absorption and fluorescent spectra (approximately 340 nm to 700 nm). Particular examples of illumination and collection wavelengths are shown in FIG. 6. Although these wavelengths have shown promise, the invention is in no way limited to the use of these wavelengths.

The measurements are made from a predetermined standoff distance from the tissue. In one embodiment constructed by the inventors to detect abnormalities on cervical tissue, the standoff distance was set to approximately 175 mm (17.5 cm) to the first optical surface of the tissue. This standoff distance can be defined by and maintained by the length of the tube 72, 172 on the tissue interface unit 70, 170.

In order to capture high-resolution spectral data from several locations in a short time (hyperspectral imaging) design compromises are required. By compromising on the spatial resolution and measurement time, fluorescence and reflectance spectra can be captured at approximately 10 nm spectral resolution according to certain embodiments.

In one embodiment of the invention used to take measurements on a subject tissue, for example, a cervix, the system uses a line-scan approach to collect data from a plurality of detection points. After positioning, measurements are made at, for example, 52, approximately 0.5-mm circular spots nominally separated from each other by approximately 3.0 mm, as shown in FIG. 5. The subject tissue is first flooded with illumination optical energy. Optical energy returned by the subject tissue is fed to a viewing device, which provides a user with an image of the tissue so that the user can appropriately position the system with respect to the subject tissue. Next, a single line or column of points on the tissue is illuminated with optical energy. According to one embodiment, the optical energy is illuminated in a range of approximately 340-700 nm. The radiation/light returned from the target tissue is collected using a coherent fiber bundle. The result is that the collected optical energy is formed into a virtual slit at the entrance of the spectrograph. The spectrograph is then used to spectrally resolve the optical energy. Given the spectral resolution required, and the dispersion by the spectrograph, in this embodiment, a single column is measured at any given time. The system sequentially scans through all eight columns shown in FIG. 5, acquiring both fluorescence and reflectance spectra in a total time duration of approximately 2 minutes.

According to another embodiment of the invention, the system uses a flood illumination approach. The subject tissue is first flooded with illumination optical energy. Optical energy returned by the subject tissue is fed to a viewing device, which provides a user with an image of the tissue so that the user can appropriately position the system with respect to the subject tissue. After positioning, the subject tissue is again flooded with illumination optical energy, for example, in a range of approximately 340-700 nm.

Figure 20A:
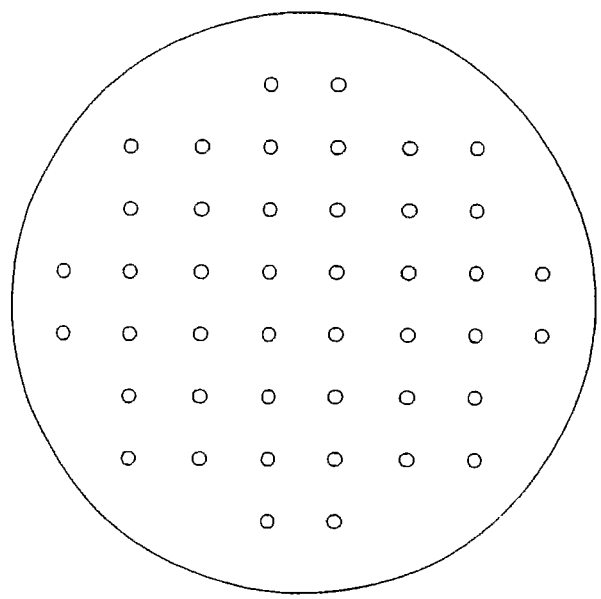
FIG. 20A is a schematic drawing of an illumination or target end of a fiber optic bundle.
Figure 20B:
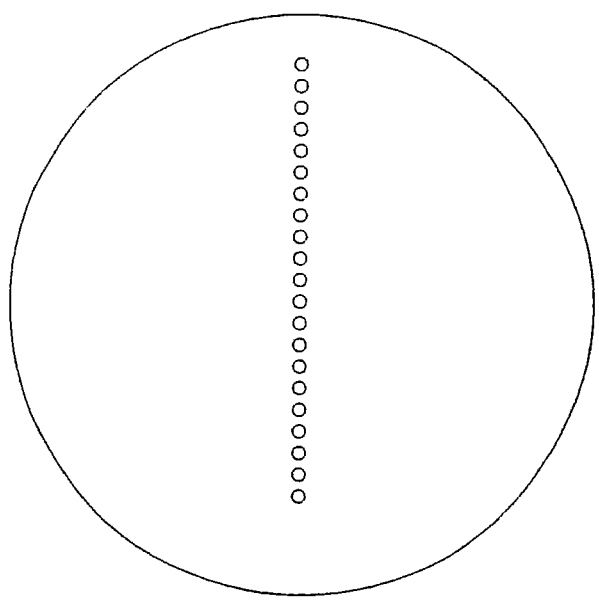
FIG. 20B is a schematic drawing of a collection end of the fiber optic bundle of FIG. 20A, illustrating a collection approach according to the invention.

The optical energy reflected and/or transmitted with respect to the subject target area is imaged with the help of a set of optics onto the face of a fiber bundle (target end) as shown in FIG. 20A. This end of the fiber bundle has fibers arranged at discrete points, as shown in FIG. 20A, and the light imaged onto the bundle at these points is transferred via the fibers to the other end of the bundle, as shown in FIG. 20B. The other end of the bundle has all of the fibers arranged in a single column. This column serves as the entrance slit of the spectrograph, which is then able to spectrally resolve, in the horizontal direction, the light in this column.

In another embodiment, the optical energy is directed to the subject target area with the help of a set of optics that images a mask of apertures onto the tissue. This is an alternative embodiment to those embodiments taught and described in FIGS. 4 and 5. The apertures are arranged in a column on the mask. The mask can be horizontally moved to scan the entire subject target area while presenting at least one single column of light at the entrance of the spectrograph at a given instant. The spectrograph is then able to spectrally resolve, in the horizontal direction according to an embodiment, the light collected by this column of apertures.

The optical energy reflected and/or transmitted by the subject tissue is then collected and directed to a diffraction grating, which separates the light spectrally. Wavelengths not of interest may be filtered out. For example, the illumination wavelength may be filtered out. The collected light is then reflected onto a device for making spectrographic measurements, such as a CCD camera and controller.

Figure 13:
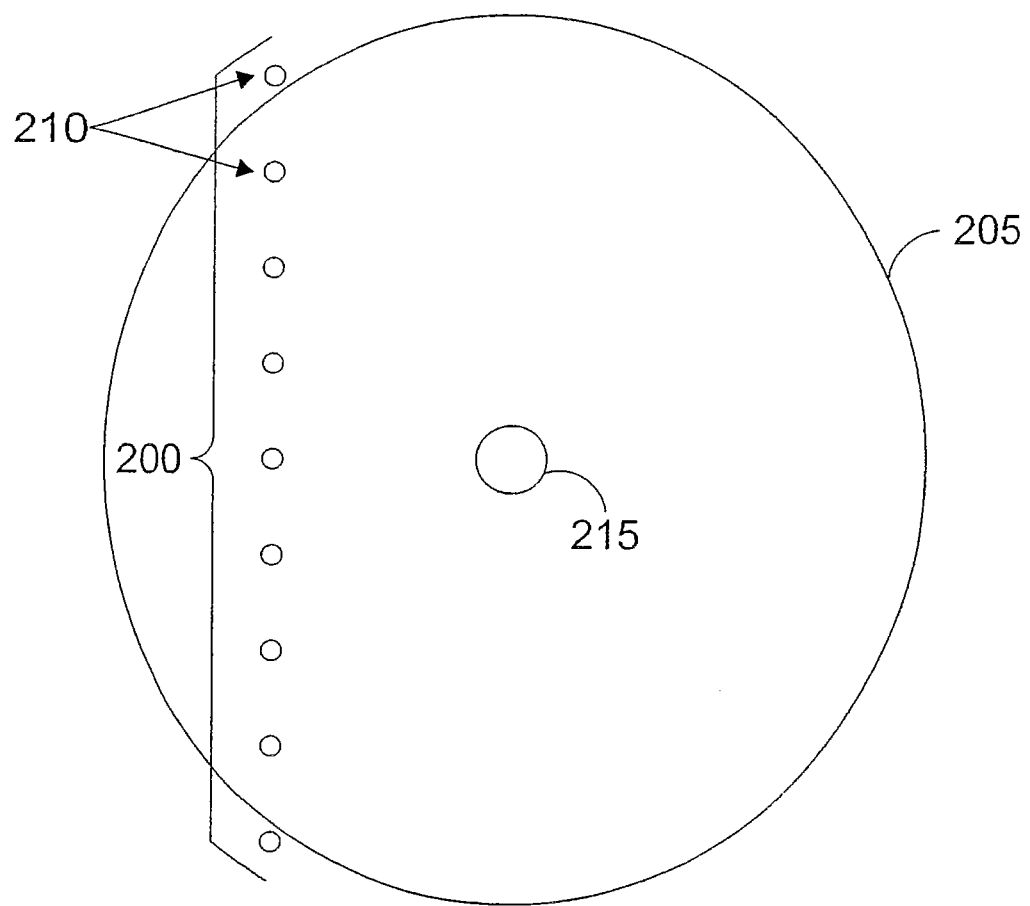
FIG. 13 is a schematic drawing showing an exemplary arrangement of detection points on a subject tissue.
Figure 14:
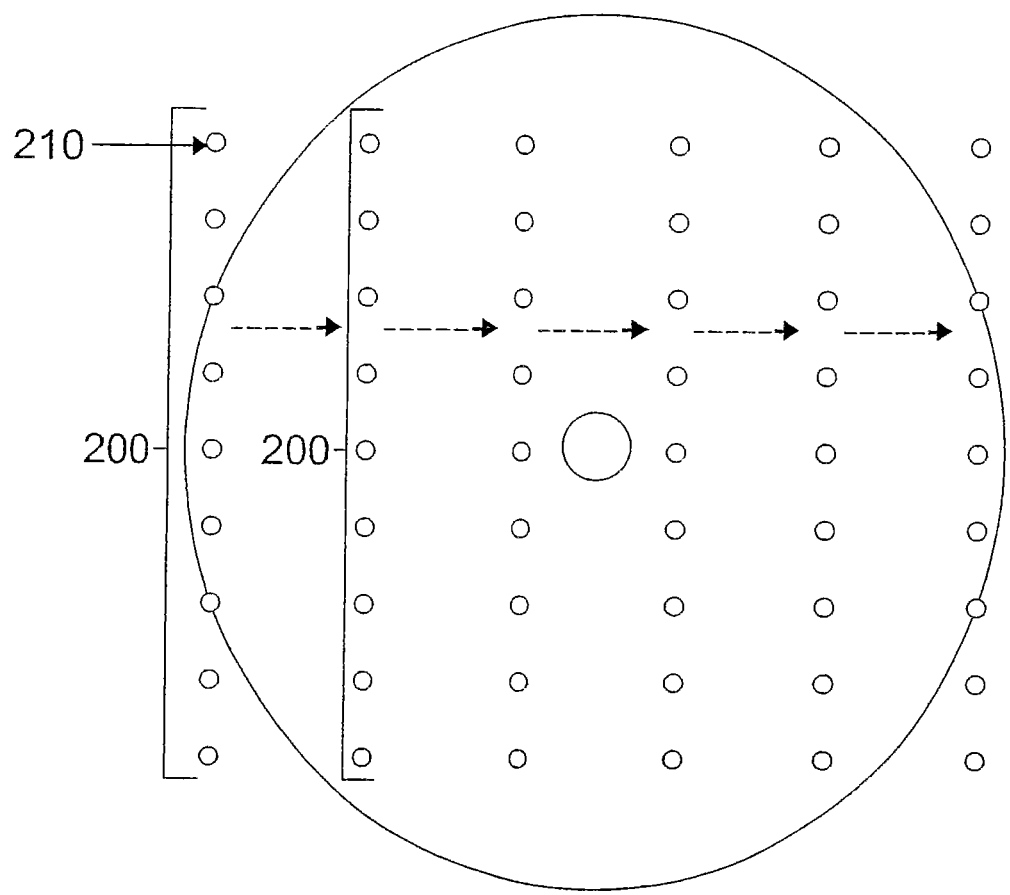
FIG. 14 is a drawing schematically showing how measurements of columns of detection points are sequentially taken across a subject tissue according to one embodiment of the invention.

As in the previous embodiments, the spectrograph only makes measurements at a single column 200 of detection points 210 at a time on a subject tissue 205, as shown in FIG. 13. According to an embodiment, reflectance measurements and fluorescence measurements are made at fifty-six points on the cervix with a separation of approximately 3 mm. However, depending on the embodiment, the number of points can vary to any number of possible points at a separation sufficient to avoid optical cross-talk/interference among the points. Reference numeral 215 represents a center of the subject tissue, in the case of a cervix this would be the Os. Measurements for various columns are then sequentially made, as shown in FIG. 14.

Figure 15:
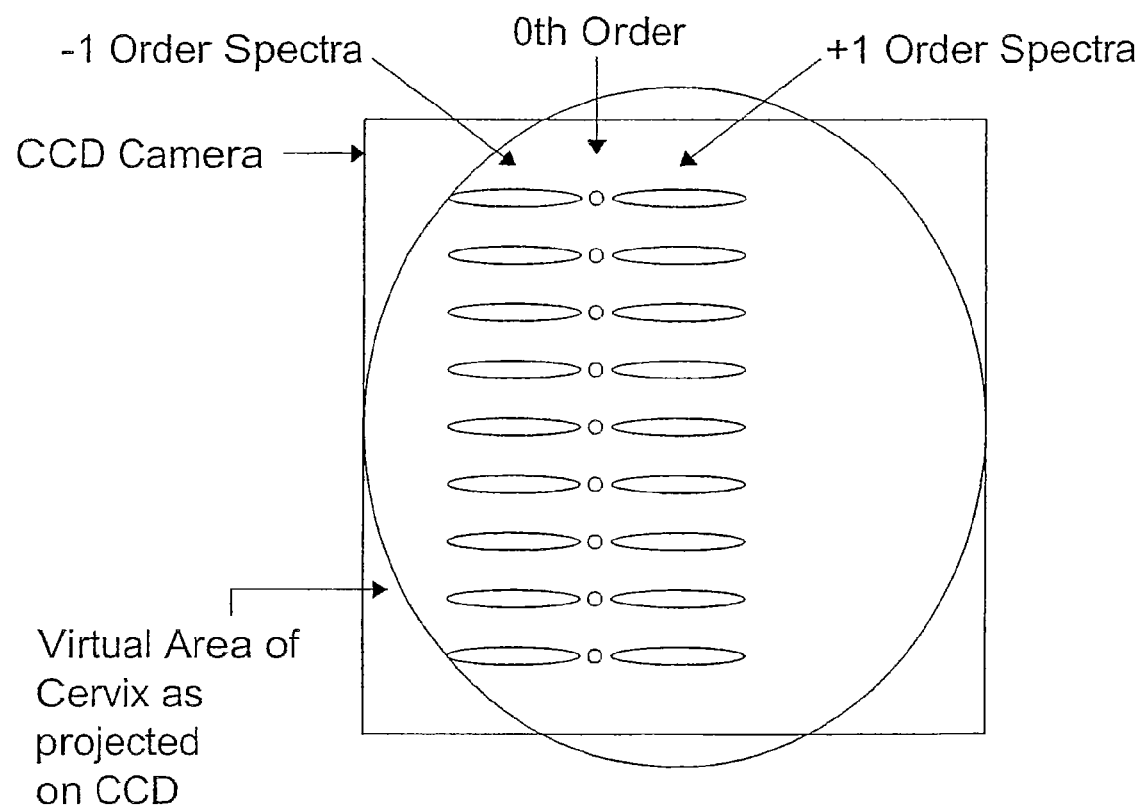
FIG. 15 is a drawing schematically showing an exemplary arrangement of a column of detection points on a CCD camera according to the invention.

FIG. 15 schematically shows what would be recorded by a CCD camera coupled to the output of a spectrograph. The light returning from a column of locations on the cervix would be spectrally resolved into different wavelengths that extend away from the column in a perpendicular direction. In other words, the pixels of the CCD camera extending to the left and the right of a single measurement position would received light of different wavelengths returned from the measurement position. The intensity of the light received at each pixel is indicative of the intensity at a particular range of wavelengths. Thus, examining the values registered at each pixel on the CCD array allows the device to determine the intensity of the light returned from each position on the illuminated column of positions at a plurality of different wavelengths.

Figure 16:
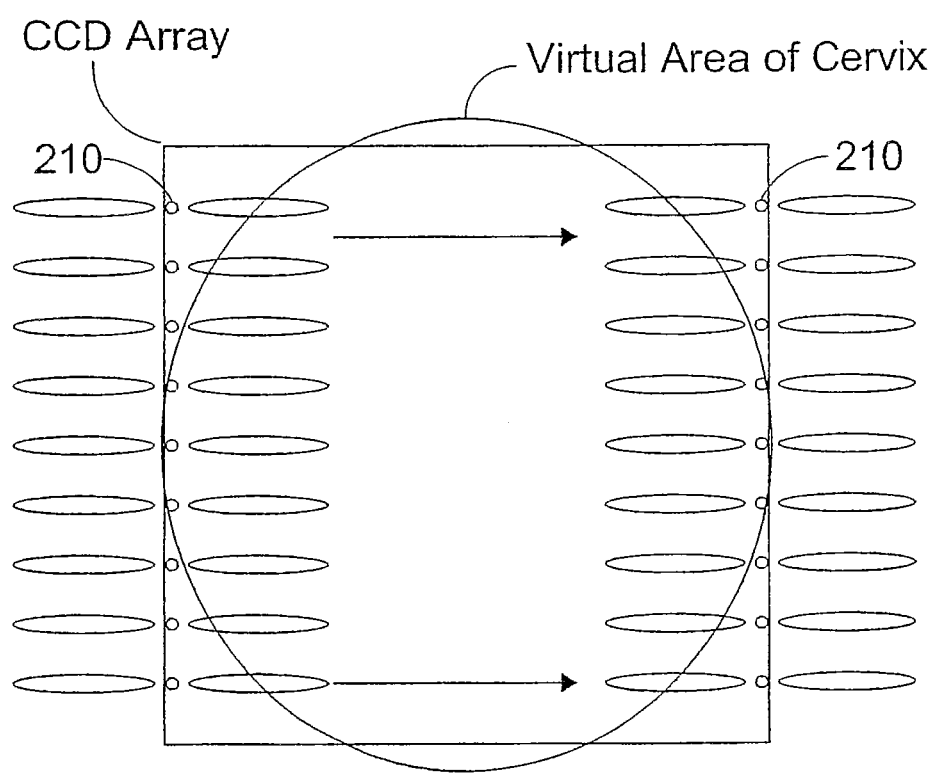
FIG. 16 is a drawing schematically showing the projection of an image across a CCD camera according to the invention.

FIG. 16 schematically shows how a series of measurements would be taken during different measurement cycles. Each measurement cycle would provide information about the light returned from a different column of illuminated positions on the target tissue.

Figure 17:
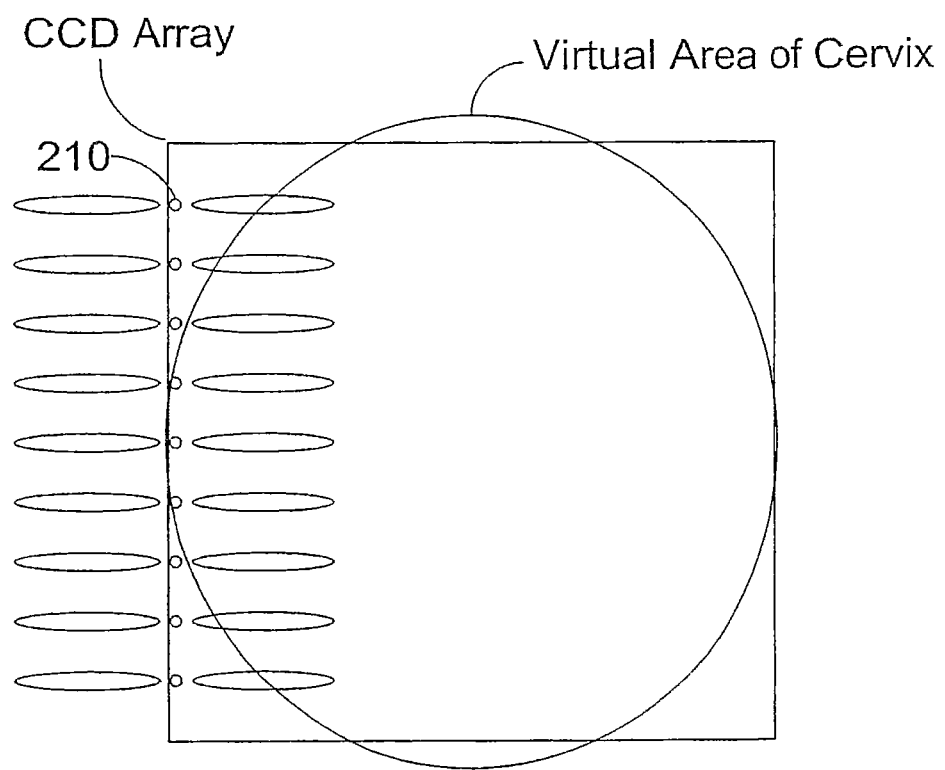
FIG. 17 is a drawing schematically showing an image of a left side of a cervix projected onto a CCD camera according to the invention.
Figure 18:
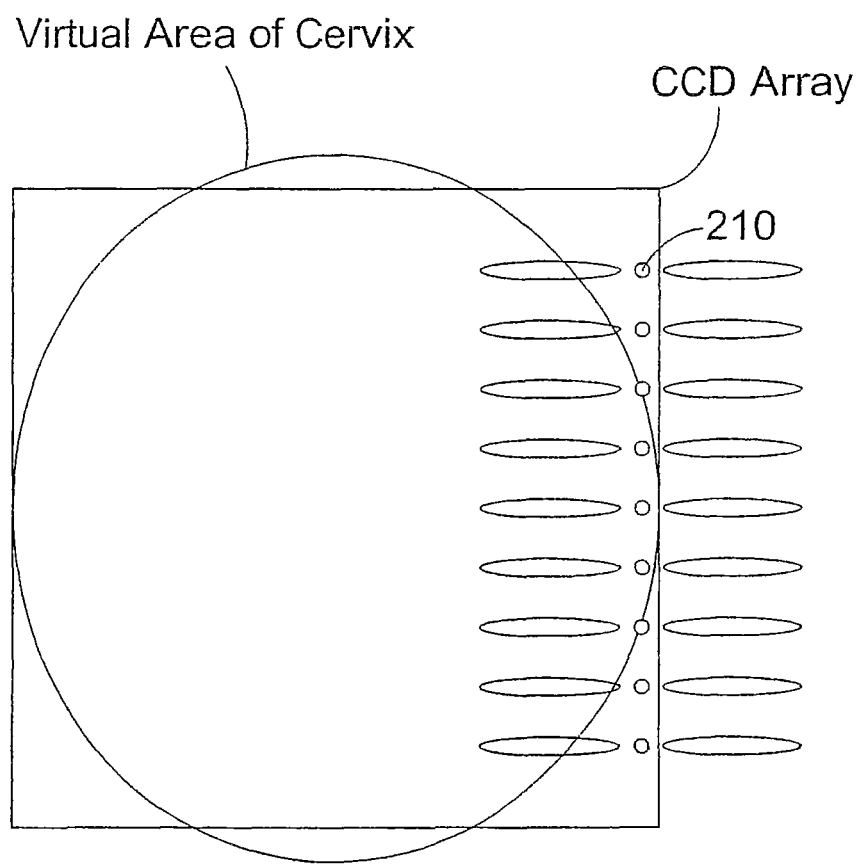
FIG. 18 is a drawing schematically showing an image of a right side of a cervix projected onto a CCD camera according to the invention.

Note, the spectrograph would separate the light from each illuminated measurement position 210 into a +1 Order Spectra and a −1 Order Spectra. Each Spectra would contain essentially the same spectral information. Thus, when interrogating a column of positions 210 on the left side of the cervix, as shown in FIG. 17, the device could utilize the +1 Order Spectra, which illuminates pixels within the CCD array. When interrogating a column of positions 210 on the right side of the cervix, as shown in FIG. 18, the device could utilize the −1 Order Spectra.

In cases where the entire spectral bandwidth is not available in either the +1 or the −1 order spectra, appropriate wavebands from both orders will be combined to form a complete spectral set.

Figure 19:
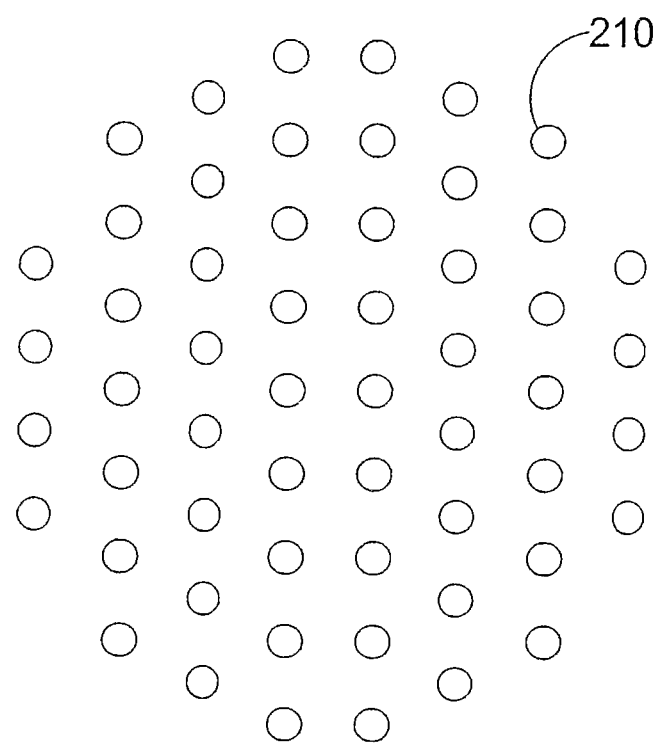
FIG. 19 is an exemplary arrangement of detection points for a cervix according to the invention.

FIG. 19 schematically shows the ultimate arrangement of detection points 210 collected for an entire cervix using this system.

The foregoing embodiments and advantages are merely exemplary and are not to be construed as limiting the present invention. The present teaching can be readily applied to other types of apparatuses and applications that may be common to those of ordinary skill in the art. The description of the present invention is intended to be illustrative, and not to limit the scope of the claims. Many alternatives, modifications, and variations will be apparent to those skilled in the art. In the claims, means-plus-function clauses are intended to cover the structures described herein as performing the recited function and not only structural equivalents but also equivalent structures.

What is claimed is:

1. An apparatus for determining tissue characteristics which indicate the presence of cancerous or pre-cancerous tissue on a patient cervix, comprising: a base unit comprising an illumination unit, a separate tissue interface unit comprising an excitation unit for delivering illumination from the illumination unit to the tissue and a detection unit capable of detecting responses in the tissue resulting from the illumination, said excitation and detection units being confocal and facing the tissue from the same side so that they converge at the tissue, a fixation stand off tube of predetermined length selected for optimal interrogation of the cervix, said tube being interposed between said units and the tissue to maintain alignment and focus with the tissue, said tube being of such diameter that it surrounds, the cervix entirely so that the tube maintains a fixed distance between the cervix and the units and so that any movement of the patient during tissue interrogation is not transmitted to the cervix so that the cervix and tube are fixed together during interrogation with the cervix surrounded by the inner periphery of the tube and whereby no portion of the interrogated tissue is blanched by the tube, said tube having a non reflective inner surface.

2. The apparatus according to claim 1, wherein said tube is detachable and has an inner peripheral diameter greater that the patient cervix so that when the tube is in contact with the cervix, patient movement is decoupled from the cervix.

3. The apparatus according to claim 1, wherein the tube is black, so that it does not create internal reflections.

4. The apparatus of claim 1, wherein said illumination and detection units are spaced from the tissue by a stand off tube having a flat black light absorbing surface and further including an imaging device capable of recording images of the tissue and wherein said detection unit is confocal with said image device, so that the image of said image unit can be spatially correlated with data from said detection unit and whereby said tube maintains said unit and image device at a fixed distance from the tissue.

5. The apparatus according to claim 1, wherein said stand off tube is flat black and large enough to surround the target tissue without interfering with its optical properties.

6. The apparatus according to claim 1, wherein said target tissue is a cervix and wherein inner peripheral contact edge of said stand off tube is sized to be of equal or larger diameter relative to the target tissue size, so that none of the target tissue is blanched by contact with the contact tube.

7. The apparatus according to claim 1, wherein the illumination unit comprises an illumination source and an illumination filter wheel said filter wheel having a plurality of filters selected to reduce artifacts due to reflected excitation, at least one filter being selected to enhance detection of reflectance and at least one filter being selected to enhance detection of fluorescence.

8. The apparatus according to claim 1, wherein the illumination unit further comprises a mask that provides for selective illumination of the target tissue, said mask including a generally vertically oriented slit having a plurality of spaced apart apertures allowing light transmission therethrough while blocking all other transmission, so that a column of a plurality of points in a single vertical line of illumination can be applied simultaneously to the target tissue and thereby more easily distinguish between normal and abnormal tissue.

9. The apparatus according to claim 8, wherein said slit is configured to move generally in steps vertically, thereby creating a plurality of discrete horizontal row measurements across target tissue.

10. The apparatus according to claim 8, wherein the detection unit includes detection points arranged into a line of discrete points spaced from each other, so that detection of the tissue is done in a line of discrete separated detection points.

11. The apparatus according to claim 8, further including a diffraction grating for receiving and resolving light received from the target tissue into spectra of different wavelengths that extend orthogonally away from the column whereby the intensity of the light detected is indicative of the intensity at a different wavelengths.

12. The apparatus according to claim 1, wherein the illumination unit further comprises a cold mirror coupled to an illumination source and an illumination filter wheel.

13. The apparatus according to claim 12, wherein the illumination unit further comprises a lens coupled to the illumination source and the illumination filter wheel.

14. The apparatus according to claim 12, wherein the illumination unit further comprises a shutter configured to selectively prevent illumination optical energy from entering the pathway that couples the base unit and the tissue interface unit.

15. The apparatus according to claim 12, wherein the illumination unit further comprises a mask that provides for selective illumination of the target tissue.

16. The apparatus according to claim 12, wherein the detection unit further comprises a spectrograph coupled to a collection filter wheel.

17. An apparatus for determining tissue characteristics which indicate the presence of cancerous or pre-cancerous tissue on a patient cervix, comprising: a base unit comprising an illumination unit, a separate tissue interface unit comprising an excitation unit for delivering illumination from the illumination unit to the tissue and a detection unit capable of detecting responses in the tissue resulting from the illumination, said excitation and detection units being confocal and facing the tissue from the same side so that they converge at the tissue;
wherein said illuminating and detecting units are spaced from the tissue and configured to illuminate said tissue in a structured illumination pattern comprising:
a tissue illuminator configured to simultaneously illuminate tissue along a band of spaced apart, generally a row of simultaneously illuminated points and measuring optical energy received from each of said points at the same time,
a line shifter configured to incrementally shift said line of points generally across the tissue, illuminating a new portion of the tissue, offset from the previous illuminated row of points, and measuring optical energy received from said points, to create a horizontal and vertical matrix of sequentially illuminated measured row of points, said points being sufficiently spaced apart along said line to minimize cross talk illumination between said points;
a diffraction grating aligned to receive said measured optical energy to create a first order spectra for measured points for determining which points on the tissue are abnormal by comparing spectral characteristics of vertically adjacent points.

18. The apparatus of claim 17, wherein the diffraction grating spreads light orthogonally to the angle of incidence thereby resolving light received from the target tissue in spectra of different wavelengths whereby the intensity of the light detected is indicative of its intensity at different wavelengths.

19. The apparatus of claim 18, wherein said diffraction grating creates elongated first order spectra which data is captured according to frequency and intensity.

20. A method of detecting cancerous or pre-cancerous cervical tissue by making time successive measurements of a patient cervix while minimizing movement and the affects of movement of the target tissue during a measurement of tissue characteristics, comprising the steps of:
a) surrounding the cervix with a hollow tube having an inner diameter at least as great as the patient cervix thereby surrounding the periphery of the cervix without substantially contacting the cervical target area so that the optical characteristics of the cervix are not affected by the blanching effect of contact therewith;
b) structurally illuminating the cervix in a plurality of spaced apart spots of light said spots forming a row of spots;
c) measuring reflected illumination from said row of spots said spots in said row being measured simultaneously;
d) measuring fluorescence illumination from said spots said spots in said row being measured simultaneously;
e) performing spectroscopic measurements on optical energy received from the target cervix from illumination;
f) moving the structured illumination to an adjacent row on the tissue to illuminate a further series of spots forming a further row and repeating steps c) d) and e) until a predetermined portion of the cervix has been interrogated, to create a plurality of spectroscopic measurements of optical energy received from the cervix from illumination sequentially in the form of a matrix of measurements taken of the cervix.

21. The method of claim 20, further including the steps of:
a) forming a second image of the target tissue;
b) comparing the first and second images to determine the degree of movement of the tissue, if any;
c) comparing the degree of movement to a predetermined standard;
d) if the movement is less than said standard, determining tissue characteristics of the target tissue based on the results of the spectroscopic measurements and wherein the step of performing spectroscopic measurements includes illuminating a first portion of a target tissue with optical energy from a first illumination source and illuminating a second portion of the target tissue with optical energy from a second illumination source.

22. The method of claim 21, wherein said diffraction grating creates elongated first order spectra which data is captured according to frequency and intensity.

23. The method of claim 20, wherein the plurality of spots detection points are separated from each other sufficiently minimize crosstalk between points.

24. The method of claim 20, wherein the tissue is contacted around the periphery of the target issue having one end in contact with the tissue and the other end being connected to an interrogation device.

25. The method of according to claim 20, wherein spectrographic measurement uses a diffraction grating to spread light orthogonally to the angle of incidence thereby resolving light received from the target tissue in spectra of different wavelengths whereby the intensity of the light detected is indicative of its intensity at different wavelengths.

* * * * *